US009943372B2

(12) United States Patent
Sholev et al.

(10) Patent No.: US 9,943,372 B2
(45) Date of Patent: Apr. 17, 2018

(54) DEVICE HAVING A WEARABLE INTERFACE FOR IMPROVING LAPAROSCOPIC SURGERY AND METHODS FOR USE THEREOF

(71) Applicants:Mordehai Sholev, Moshav Amikam (IL); Gal Atarot, Kfar Saba (IL); Motti Frimer, Zichron Yaakov (IL)

(72) Inventors: Mordehai Sholev, Moshav Amikam (IL); Gal Atarot, Kfar Saba (IL); Motti Frimer, Zichron Yaakov (IL)

(73) Assignee: M.S.T. MEDICAL SURGERY TECHNOLOGIES LTD., Yoqneam (IL)

( * ) Notice: Subject to any disclaimer, the term of this patent is extended or adjusted under 35 U.S.C. 154(b) by 273 days.

(21) Appl. No.: 13/736,118

(22) Filed: Jan. 8, 2013

(65) Prior Publication Data

US 2013/0123804 A1   May 16, 2013
US 2017/0281275 A9   Oct. 5, 2017

Related U.S. Application Data

(63) Continuation-in-part of application No. 11/874,534, filed on Oct. 18, 2007, now Pat. No. 9,295,379, and
(Continued)

(51) Int. Cl.
*A61B 1/00* (2006.01)
*A61B 1/04* (2006.01)
(Continued)

(52) U.S. Cl.
CPC .......... *A61B 34/10* (2016.02); *A61B 1/00016* (2013.01); *G08C 17/02* (2013.01)

(58) Field of Classification Search
CPC ............ A61B 1/00016; A61B 1/00039; A61B 1/00149; A61B 19/22; A61B 2019/2207; A61B 2019/2211; A61B 2019/2215
(Continued)

(56) References Cited

U.S. PATENT DOCUMENTS 4,559,928 A * 12/1985 Takayama ..................... 600/152
4,756,204 A   7/1988 Wittwer et al.
(Continued)

FOREIGN PATENT DOCUMENTS

AU   2007234510 A1   12/2007
AU   2013202775 A1   12/2013
(Continued)

OTHER PUBLICATIONS

Atarot et al., Manual Control System for Maneuvering an Endoscope, co-pending U.S. Appl. No. 14/380,082, filed Aug. 21, 2014, 118 pages.
(Continued)

*Primary Examiner* — Anhtuan T Nguyen
*Assistant Examiner* — William Chou

(57) ABSTRACT

A device for controlling an endoscope system for laparoscopic surgery. The device includes a wearable interface and an automated assistant for maneuvering an endoscope to a desired location, and at least one wearable operator. The wearable operator includes a transmitter that is in communication with at least one instrument. The system also includes a wireless receiver to receive signals from the transmitter and a computerized laparoscopy system that is in communication with the wireless receiver and that provides a visual depiction of a selected instrument.

9 Claims, 17 Drawing Sheets

Related U.S. Application Data a continuation of application No. PCT/IL2012/000312, filed on Aug. 21, 2012.

(51) Int. Cl.
    *A61B 1/06*     (2006.01)
    *A61B 34/10*     (2016.01)
    *G08C 17/02*     (2006.01)

(58) Field of Classification Search
    USPC ........ 600/118, 103, 102, 114, 117, 424, 429,
                 600/101, 109, 160, 173; 606/130, 1
    See application file for complete search history.

(56) References Cited

U.S. PATENT DOCUMENTS

| | | | | |
|---|---|---|---|---|
| 4,854,301 | A | 8/1989 | Nakajima | |
| 4,955,891 | A * | 9/1990 | Carol | 606/130 |
| 5,086,401 | A | 2/1992 | Glassman et al. | |
| 5,154,723 | A * | 10/1992 | Kubota et al. | 606/130 |
| 5,201,742 | A * | 4/1993 | Hasson | 606/130 |
| 5,211,165 | A | 5/1993 | Dumoulin et al. | |
| 5,269,305 | A * | 12/1993 | Corol | 600/429 |
| 5,313,306 | A | 5/1994 | Kuban et al. | |
| 5,494,034 | A | 2/1996 | Schlondorff et al. | |
| 5,553,198 | A | 9/1996 | Wang et al. | |
| 5,571,072 | A * | 11/1996 | Kronner | 600/102 |
| 5,572,999 | A * | 11/1996 | Funda et al. | 600/118 |
| 5,749,362 | A | 5/1998 | Funda et al. | |
| 5,820,623 | A | 10/1998 | Ng | |
| 5,836,869 | A * | 11/1998 | Kudo | A61B 1/00039 600/102 |
| 5,876,325 | A * | 3/1999 | Mizuno | A61B 1/00048 600/102 |
| 5,878,193 | A * | 3/1999 | Wang et al. | 700/251 |
| 5,911,036 | A | 6/1999 | Wright et al. | |
| 5,971,976 | A | 10/1999 | Wang et al. | |
| 6,024,695 | A * | 2/2000 | Taylor et al. | 600/102 |
| 6,100,501 | A * | 8/2000 | von der Heyde | 219/229 |
| 6,106,511 | A * | 8/2000 | Jensen | 606/1 |
| 6,179,776 | B1 | 1/2001 | Adams et al. | |
| 6,192,267 | B1 | 2/2001 | Scherninski et al. | |
| 6,368,332 | B1 | 4/2002 | Salcudean et al. | |
| 6,387,044 | B1 | 5/2002 | Tachibana et al. | |
| 6,451,027 | B1 * | 9/2002 | Cooper et al. | 606/130 |
| 6,591,239 | B1 | 7/2003 | McCall et al. | |
| 6,632,170 | B1 | 10/2003 | Bohanan et al. | |
| 6,714,841 | B1 * | 3/2004 | Wright et al. | 700/259 |
| 6,723,106 | B1 * | 4/2004 | Charles et al. | 606/130 |
| 6,747,566 | B2 | 6/2004 | Hou | |
| 6,785,358 | B2 | 8/2004 | Johnson et al. | |
| 6,786,896 | B1 | 9/2004 | Madhani et al. | |
| 6,837,883 | B2 | 1/2005 | Moll et al. | |
| 6,850,794 | B2 | 2/2005 | Shahidi | |
| 6,946,812 | B1 * | 9/2005 | Martin et al. | 318/567 |
| 6,997,866 | B2 * | 2/2006 | Payandeh et al. | 600/102 |
| 7,048,745 | B2 * | 5/2006 | Tierney et al. | 606/130 |
| 7,087,049 | B2 | 8/2006 | Nowlin et al. | |
| 7,286,992 | B2 | 10/2007 | Sander et al. | |
| 7,313,430 | B2 * | 12/2007 | Urquhart et al. | 600/429 |
| 7,319,897 | B2 | 1/2008 | Leitner et al. | |
| 7,674,270 | B2 * | 3/2010 | Layer | 606/130 |
| 7,833,152 | B2 | 11/2010 | Chatenever et al. | |
| 8,058,969 | B1 | 11/2011 | Lai et al. | |
| 8,079,950 | B2 | 12/2011 | Stern et al. | |
| 8,100,133 | B2 | 1/2012 | Mintz et al. | |
| 8,123,675 | B2 | 2/2012 | Funda et al. | |
| 8,170,717 | B2 | 5/2012 | Sutherland et al. | |
| 8,224,484 | B2 | 7/2012 | Swarup et al. | |
| 8,256,319 | B2 | 9/2012 | Cooper et al. | |
| 8,388,516 | B2 | 3/2013 | Sholev | |
| 8,414,475 | B2 | 4/2013 | Sholev | |
| 8,435,171 | B2 | 5/2013 | Sholev | |
| 8,690,755 | B2 | 4/2014 | Sholev | |
| 8,702,590 | B2 | 4/2014 | Sholev | |
| 8,758,263 | B1 | 6/2014 | Rahimian et al. | |
| 8,992,542 | B2 | 3/2015 | Hagag et al. | |
| 9,002,518 | B2 | 4/2015 | Manzo et al. | |
| 9,204,939 | B2 | 12/2015 | Frimer et al. | |
| 9,295,379 | B2 | 3/2016 | Sholev | |
| 9,504,456 | B2 | 11/2016 | Frimer et al. | |
| 9,757,204 | B2 | 9/2017 | Frimer et al. | |
| 9,757,206 | B2 | 9/2017 | Frimer et al. | |
| 2002/0026096 | A1 | 2/2002 | Motoki et al. | |
| 2002/0082612 | A1 * | 6/2002 | Moll et al. | 606/130 |
| 2002/0091301 | A1 | 7/2002 | Levin | |
| 2002/0097332 | A1 | 7/2002 | Lee et al. | |
| 2002/0111713 | A1 | 8/2002 | Wang et al. | |
| 2002/0133174 | A1 * | 9/2002 | Charles et al. | 606/130 |
| 2002/0151795 | A1 | 10/2002 | Palti | |
| 2002/0166403 | A1 | 11/2002 | Choset et al. | |
| 2002/0167422 | A1 | 11/2002 | Andre et al. | |
| 2003/0055410 | A1 * | 3/2003 | Evans et al. | 606/1 |
| 2003/0062858 | A1 | 4/2003 | Shimizu et al. | |
| 2003/0195389 | A1 | 10/2003 | Motoki et al. | |
| 2003/0216833 | A1 | 11/2003 | Mukai et al. | |
| 2003/0233102 | A1 * | 12/2003 | Nakamura et al. | 606/130 |
| 2004/0015053 | A1 | 1/2004 | Bieger et al. | |
| 2004/0024387 | A1 * | 2/2004 | Payandeh et al. | 606/1 |
| 2004/0089777 | A1 | 5/2004 | Schilt et al. | |
| 2004/0111183 | A1 | 6/2004 | Sutherland et al. | |
| 2004/0138524 | A1 | 7/2004 | Ueda et al. | |
| 2004/0162564 | A1 * | 8/2004 | Charles et al. | 606/130 |
| 2004/0204627 | A1 * | 10/2004 | Furukawa | 600/118 |
| 2004/0239631 | A1 | 12/2004 | Gresham | |
| 2005/0043718 | A1 * | 2/2005 | Madhani et al. | 606/1 |
| 2005/0090711 | A1 | 4/2005 | Fuchs et al. | |
| 2005/0119527 | A1 | 6/2005 | Banik et al. | |
| 2005/0123189 | A1 | 6/2005 | Bayer et al. | |
| 2005/0162383 | A1 * | 7/2005 | Rosenberg | 345/156 |
| 2005/0171557 | A1 * | 8/2005 | Shoham | 606/130 |
| 2005/0219552 | A1 | 10/2005 | Ackerman et al. | |
| 2005/0272971 | A1 | 12/2005 | Ohnishi et al. | |
| 2005/0273086 | A1 * | 12/2005 | Green et al. | 606/1 |
| 2006/0100501 | A1 * | 5/2006 | Berkelman et al. | 600/415 |
| 2006/0142657 | A1 | 6/2006 | Quaid et al. | |
| 2006/0167440 | A1 * | 7/2006 | Cooper et al. | 606/1 |
| 2006/0217206 | A1 | 9/2006 | Thompson | |
| 2006/0281971 | A1 | 12/2006 | Sauer et al. | |
| 2007/0005045 | A1 | 1/2007 | Mintz et al. | |
| 2007/0013336 | A1 | 1/2007 | Nowlin et al. | |
| 2007/0021713 | A1 | 1/2007 | Kumar et al. | |
| 2007/0021752 | A1 | 1/2007 | Rogers | |
| 2007/0088340 | A1 * | 4/2007 | Brock et al. | 606/1 |
| 2007/0142701 | A1 | 6/2007 | Goldberg et al. | |
| 2007/0142824 | A1 | 6/2007 | Devengenzo et al. | |
| 2007/0142968 | A1 | 6/2007 | Prisco et al. | |
| 2007/0156017 | A1 * | 7/2007 | Lamprecht et al. | 600/102 |
| 2007/0265527 | A1 * | 11/2007 | Wohlgemuth | 600/424 |
| 2007/0299427 | A1 | 12/2007 | Yeung et al. | |
| 2008/0004603 | A1 | 1/2008 | Larkin et al. | |
| 2008/0039256 | A1 | 2/2008 | Jinno et al. | |
| 2008/0046122 | A1 | 2/2008 | Manzo et al. | |
| 2008/0071140 | A1 | 3/2008 | Gattani et al. | |
| 2008/0091066 | A1 * | 4/2008 | Sholev | 600/112 |
| 2008/0091302 | A1 * | 4/2008 | Sholev | 700/245 |
| 2008/0108872 | A1 | 5/2008 | Glukhovsky et al. | |
| 2008/0114376 | A1 | 5/2008 | Steinberg | |
| 2008/0154389 | A1 | 6/2008 | Smith et al. | |
| 2008/0207997 | A1 | 8/2008 | Higgins et al. | |
| 2008/0215181 | A1 | 9/2008 | Smith et al. | |
| 2008/0234866 | A1 | 9/2008 | Kishi et al. | |
| 2008/0262297 | A1 | 10/2008 | Gilboa et al. | |
| 2008/0275452 | A1 | 11/2008 | Lang et al. | |
| 2008/0300453 | A1 | 12/2008 | Aoki et al. | |
| 2008/0312540 | A1 | 12/2008 | Ntziachristos | |
| 2009/0018419 | A1 | 1/2009 | Torch | |
| 2009/0043310 | A1 | 2/2009 | Rasmussen | |
| 2009/0048611 | A1 | 2/2009 | Funda et al. | |
| 2009/0062813 | A1 * | 3/2009 | Prisco et al. | 606/130 |
| 2009/0088634 | A1 * | 4/2009 | Zhao et al. | 600/427 |
| 2009/0088773 | A1 * | 4/2009 | Zhao et al. | 606/130 |
| 2009/0088774 | A1 | 4/2009 | Swarup et al. | |
| 2009/0088897 | A1 * | 4/2009 | Zhao et al. | 700/250 |

(56) References Cited

U.S. PATENT DOCUMENTS

| | | |
|---|---|---|
| 2009/0099520 A1 | 4/2009 | Millman et al. |
| 2009/0171373 A1 | 7/2009 | Farritor et al. |
| 2009/0177032 A1 | 7/2009 | Garibaldi et al. |
| 2009/0216114 A1 | 8/2009 | Gorges et al. |
| 2009/0240259 A1 | 9/2009 | Nelson et al. |
| 2009/0248037 A1 | 10/2009 | Prisco |
| 2009/0312101 A1 | 12/2009 | Pope |
| 2009/0312600 A1* | 12/2009 | Sholev .................... 600/102 |
| 2010/0022871 A1 | 1/2010 | De Beni et al. |
| 2010/0036198 A1 | 2/2010 | Tacchino et al. |
| 2010/0063630 A1 | 3/2010 | Sutherland et al. |
| 2010/0121149 A1 | 5/2010 | Sholev |
| 2010/0185211 A1 | 7/2010 | Herman et al. |
| 2010/0185212 A1 | 7/2010 | Sholev |
| 2010/0234857 A1 | 9/2010 | Itkowitz et al. |
| 2010/0274079 A1 | 10/2010 | Kim et al. |
| 2011/0069160 A1 | 3/2011 | Ning |
| 2011/0082587 A1 | 4/2011 | Ziaei et al. |
| 2011/0118748 A1 | 5/2011 | Itkowitz |
| 2011/0144659 A1 | 6/2011 | Sholev |
| 2011/0175989 A1 | 7/2011 | Islam |
| 2011/0177469 A1 | 7/2011 | Suter et al. |
| 2011/0257475 A1* | 10/2011 | Berkelman et al. .......... 600/102 |
| 2012/0020547 A1 | 1/2012 | Zhao et al. |
| 2012/0029277 A1 | 2/2012 | Sholev |
| 2012/0041263 A1 | 2/2012 | Sholev |
| 2012/0071893 A1 | 3/2012 | Smith et al. |
| 2012/0245415 A1 | 9/2012 | Emura et al. |
| 2013/0063580 A1 | 3/2013 | Ogawa et al. |
| 2013/0123804 A1 | 5/2013 | Sholev et al. |
| 2013/0204271 A1 | 8/2013 | Brisson et al. |
| 2014/0005489 A1 | 1/2014 | Charles |
| 2014/0052005 A1 | 2/2014 | Yokota |
| 2014/0066703 A1 | 3/2014 | Blumenkranz et al. |
| 2014/0142592 A1 | 5/2014 | Moon et al. |
| 2014/0163359 A1 | 6/2014 | Sholev et al. |
| 2014/0194896 A1 | 7/2014 | Frimer et al. |
| 2014/0221738 A1 | 8/2014 | Sholev et al. |
| 2014/0228632 A1 | 8/2014 | Sholev et al. |
| 2014/0378763 A1 | 12/2014 | Atarot et al. |
| 2015/0025549 A1 | 1/2015 | Kilroy et al. |
| 2015/0031953 A1 | 1/2015 | Atarot et al. |
| 2015/0238276 A1 | 8/2015 | Atarot et al. |
| 2015/0366433 A1 | 12/2015 | Atarot et al. |
| 2016/0007826 A1 | 1/2016 | Frimer et al. |
| 2016/0007827 A1 | 1/2016 | Frimer et al. |
| 2016/0007828 A1 | 1/2016 | Frimer et al. |
| 2016/0015473 A1 | 1/2016 | Frimer et al. |
| 2016/0051336 A1 | 2/2016 | Frimer et al. |
| 2016/0174817 A1 | 6/2016 | Frimer et al. |
| 2016/0174955 A1 | 6/2016 | Frimer et al. |
| 2016/0184031 A1 | 6/2016 | Sholev et al. |
| 2016/0242631 A1 | 8/2016 | Sholev |
| 2016/0270864 A1 | 9/2016 | Frimer et al. |
| 2016/0345802 A1 | 12/2016 | Nir et al. |
| 2017/0027654 A1 | 2/2017 | Frimer |
| 2017/0049521 A1 | 2/2017 | Sholev et al. |
| 2017/0105713 A1 | 4/2017 | Frimer et al. |
| 2017/0172382 A1 | 6/2017 | Nir et al. |
| 2017/0202624 A1 | 7/2017 | Atarot et al. |

FOREIGN PATENT DOCUMENTS

| | | |
|---|---|---|
| CN | 203042209 U | 7/2013 |
| EP | 1681029 A1 | 7/2006 |
| EP | 2208463 A1 | 7/2010 |
| EP | 2246006 A2 | 11/2010 |
| EP | 2347785 A1 | 7/2011 |
| IL | 184664 A | 2/2015 |
| JP | 6063003 A | 3/1994 |
| KR | 20090123260 A | 12/2009 |
| WO | WO1996009587 A1 | 3/1996 |
| WO | WO2003007834 A1 | 1/2003 |
| WO | WO2003094759 A1 | 11/2003 |
| WO | WO2006039646 A2 | 4/2006 |
| WO | WO2006111966 A2 | 10/2006 |
| WO | WO2008035345 A2 | 3/2008 |
| WO | WO2009004616 A2 | 1/2009 |
| WO | WO2009010980 A1 | 1/2009 |
| WO | WO2010122563 A1 | 10/2010 |
| WO | WO2011088400 A2 | 7/2011 |
| WO | WO2013027200 A2 | 2/2013 |
| WO | WO2013027201 A2 | 2/2013 |
| WO | WO2013027202 A2 | 2/2013 |
| WO | WO2013027203 A1 | 2/2013 |
| WO | WO2013042107 A1 | 3/2013 |
| WO | WO2013128457 A1 | 9/2013 |
| WO | WO2013132501 A1 | 9/2013 |
| WO | WO2014049598 A1 | 4/2014 |
| WO | WO2014108898 A1 | 7/2014 |
| WO | WO2015151094 A1 | 10/2015 |
| WO | WO2015151098 A3 | 12/2015 |
| WO | WO2015189839 A1 | 12/2015 |
| WO | WO2016005988 A1 | 1/2016 |

OTHER PUBLICATIONS

Atarot et al., Overall Endoscopic Control System, co-pending U.S. Appl. No. 14/380,086, filed Sep. 16, 2014, 79 pages.
International Preliminary Report on Patentability (Chapter I) for PCT/IL2014/050022, dated Jul. 14, 2015.
International Preliminary Report on Patentability (Chapter I) for PCT/IL2013/050183, dated Sep. 2, 2014.
International Preliminary Report on Patentability (Chapter I) for PCT/IL2013/050216, dated Sep. 9, 2014.
International Preliminary Report on Patentability (Chapter I) for PCT/IL2015/050345, dated Oct. 4, 2016.
International Preliminary Report on Patentability (Chapter I) for PCT/IL2015/050349, dated Oct. 4, 2016.
International Preliminary Report on Patentability (Chapter I) for PCT/IL2006/000478, dated Oct. 23, 2007.
International Preliminary Report on Patentability (Chapter I) for PCT/IL2010/000330, dated Oct. 25, 2011.
International Preliminary Report on Patentability (Chapter II) for PCT/IL2015/050579, dated Jun. 2, 2016.
International Preliminary Report on Patentability (Chapter II) for PCT/IL2008/000994, dated Jun. 10, 2009.
International Search Report for PCT/IL2012/000312, dated Jan. 8, 2013.
International Search Report for PCT/IL2013/050806, dated Feb. 10, 2014.
International Search Report for PCT/IL2012/000311, dated Feb. 13, 2013.
International Search Report for PCT/IL2012/000342, dated Feb. 25, 2013.
International Search Report for PCT/IL2012/000310, dated Feb. 28, 2013.
International Search Report for PCT/IL2008/000902, dated Mar. 2, 2009.
International Search Report for PCT/IL2014/050022, dated May 12, 2014.
International Search Report for PCT/IL2013/050183, dated Jun. 28, 2013.
International Search Report for PCT/IL2010/000330, dated Aug. 10, 2010.
International Search Report for PCT/IL2013/050216, dated Aug. 20, 2013.
International Search Report for PCT/IL2015/050345, dated Sep. 2, 2015.
International Search Report for PCT/IL2006/000478, dated Sep. 5, 2007.
International Search Report for PCT/IL2007/001161, dated Sep. 12, 2008.
International Search Report for PCT/IL2015/050579, dated Nov. 2, 2015.
International Search Report for PCT/IL2015/050349, dated Nov. 4, 2015.
International Search Report for PCT/IL2012/000309 dated Feb. 7, 2013.

(56) References Cited

OTHER PUBLICATIONS

International Search Report for PCT/IL2015/050718, dated Nov. 10, 2015.
International Search Report for PCT/IL2008/000994, dated Dec. 1, 2008.
Response dated Jan. 9, 2015, to Non-Final Rejection Office Action issued by the USPTO for the U.S. Appl. No. 13/265,206, dated Aug. 13, 2014.
Response dated Jan. 10, 2013, to Final Rejection Office Action issued by the USPTO for the U.S. Appl. No. 12/441,838, dated Nov. 21, 2012.
Response dated Feb. 3, 2014, to Restriction Requirement Office Action issued by the USPTO for the U.S. Appl. No. 13/265,206, dated Dec. 2, 2013.
Response dated Feb. 8, 2017, to Final Rejection Office Action issued by the USPTO for the U.S. Appl. No. 14/154,225, dated Aug. 15, 2016.
Response dated Feb. 8, 2017, to Non-Final Rejection Office Action issued by the USPTO for the U.S. Appl. No. 15/086,194, dated Aug. 19, 2016.
Response dated Feb. 21, 2013, to Advisory Action issued by the USPTO for the U.S. Appl. No. 12/441,838, dated Feb. 21, 2013.
Response dated Mar. 31, 2016, to Final Rejection Office Action issued by the USPTO for the U.S. Appl. No. 13/265,206, dated Mar. 16, 2016.
Response dated Apr. 3, 2013, to Non-Final Rejection Office Action issued by the USPTO for the U.S. Appl. No. 12/667,420, dated Jan. 23, 2013.
Response dated Dec. 16, 2012, to Non-Final Rejection Office Action issued by the USPTO for the U.S. Appl. No. 12/652,131, dated Jun. 15, 2012.
Response dated May 14, 2012, to Non-Final Rejection Office Action issued by the USPTO for the U.S. Appl. No. 12/441,838, dated Feb. 13, 2012.
Response dated Jun. 1, 2016, to Non-Final Rejection Office Action issued by the USPTO for the U.S. Appl. No. 14/752,947, dated Mar. 18, 2016.
Response dated Jun. 21, 2015, to Non-Final Rejection Office Action issued by the USPTO for the U.S. Appl. No. 14/150,939, dated Apr. 17, 2015.
Response dated Jul. 14, 2014, to Restriction Requirement Office Action issued by the USPTO for the U.S. Appl. No. 13/736,118, dated Apr. 17, 2014.
Response dated Aug. 6, 2015, to Miscellaneous Office Action issued by the USPTO for the U.S. Appl. No. 13/265,206, dated Jun. 22, 2015.
Response dated Aug. 6, 2015, to Restriction Requirement Office Action issued by the USPTO for the U.S. Appl. No. 14/239,997, dated May 16, 2016.
Response dated Sep. 10, 2013, to Final Rejection Office Action issued by the USPTO for the U.S. Appl. No. 12/667,420, dated Aug. 1, 2013.
Response dated Oct. 10, 2013, to Non-Final Rejection Office Action issued by the USPTO for the U.S. Appl. No. 12/441,838, dated Aug. 16, 2013.
Response dated Oct. 10, 2016, to Non-Final Rejection Office Action issued by the USPTO for the U.S. Appl. No. 14/239,897, dated Apr. 26, 2016.
Response dated Nov. 24, 2016, to Non-Final Rejection Office Action issued by the USPTO for the U.S. Appl. No. 14/753,902, dated Jun. 7, 2016.
Response dated Nov. 18, 2015, to Restriction Requirement Office Action issued by the USPTO for the U.S. Appl. No. 14/154,225, dated Sep. 24, 2015.
Response dated Nov. 24, 2016, to Non-Final Rejection Office Action issued by the USPTO for the U.S. Appl. No. 14/752,949, dated Jun. 7, 2015.
Arshak et al. "A Model for Estimating the Real-Time Positions of a moving Object in Wireless Telemetry Applications using RF Sensors.", Sensors Applications Symposium (SAS), 2007, IEEE Sensors Applications Symposium, San Diego, California, USA, Feb. 6-8, 2008, pp. 1-6.
Advisory Action issued by the USPTO for the U.S. Appl. No. 12/441,838, dated Feb. 1, 2011.
Ex Parte Quayle Action issued by the USPTO for the U.S. Appl. No. 13/265,206, dated Mar. 14, 2017.
Final Rejection Office Action issued by the USPTO for the U.S. Appl. No. 14/239,897, dated Jan. 26, 2017.
Final Rejection Office Action issued by the USPTO for the U.S. Appl. No. 15/086,194, dated Feb. 27, 2017.
Final Rejection Office Action issued by the USPTO for the U.S. Appl. No. 13/265,206, dated Mar. 16, 2016.
International Preliminary Report on Patentability (Chapter I) for PCT/IL2012/000311, dated Jul. 14, 2015.
Final Rejection Office Action issued by the USPTO for the U.S. Appl. No. 12/667,420, dated Aug. 1, 2013.
Final Rejection Office Action issued by the USPTO for the U.S. Appl. No. 14/154,225 dated Aug. 15, 2016.
Final Rejection Office Action issued by the USPTO for the U.S. Appl. No. 12/441,838, dated Nov. 21, 2012.
Miscellaneous Office Action issued by the USPTO for the U.S. Appl. No. 13/265,206, dated Jun. 22, 2015.
Non-Final Rejection Office Action issed by the USPTO for the U.S. Appl. No. 14/154,225, dated Jan. 11, 2016.
Non-Final Rejection Office Action issed by the USPTO for the U.S. Appl. No. 12/667,420, dated Jan. 23, 2013.
Non-Final Rejection Office Action issed by the USPTO for the U.S. Appl. No. 14/816,099, dated Jan. 26, 2017.
Non-Final Rejection Office Action issed by the USPTO for the U.S. Appl. No. 14/816,127, dated Jan. 26, 2017.
Non-Final Rejection Office Action issed by the USPTO for the U.S. Appl. No. 14/817,245, dated Feb. 8, 2017.
Non-Final Rejection Office Action issed by the USPTO for the U.S. Appl. No. 12/441,838, dated Feb. 13, 2012.
Non-Final Rejection Office Action issed by the USPTO for the U.S. Appl. No. 15/169,990, dated Feb. 24, 2017.
Non-Final Rejection Office Action issed by the USPTO for the U.S. Appl. No. 14/752,947, dated Mar. 18, 2016.
Non-Final Rejection Office Action issed by the USPTO for the U.S. Appl. No. 14/150,939, dated Apr. 17, 2015.
Non-Final Rejection Office Action issed by the USPTO for the U.S. Appl. No. 14/239,897, dated Apr. 26, 2016.
Non-Final Rejection Office Action issed by the USPTO for the U.S. Appl. No. 14/752,949, dated Jun. 7, 2015.
Non-Final Rejection Office Action issed by the USPTO for the U.S. Appl. No. 12/652,131, dated Jun. 15, 2012.
Non-Final Rejection Office Action issued by the USPTO for the U.S. Appl. No. 14/753,902, dated Jun. 16, 2016.
Non-Final Rejection Office Action issued by the USPTO for the U.S. Appl. No. 13/265,206, dated Aug. 13, 2014.
International Preliminary Report on Patentability (Chapter I) for PCT/IL2007/001161, dated Apr. 7, 2009.
Non-Final Rejection Office Action issued by the USPTO for the U.S. Appl. No. 15/086,194, dated Aug. 19, 2016.
Non-Final Rejection Office Action issued by the USPTO for the U.S. Appl. No. 14/817,223, dated Oct. 7, 2016.
Final Rejection Office Action issued by the USPTO for the U.S. Appl. No. 12/441,838, dated Nov. 12, 2013.
Non-Final Rejection Office Action issued by the USPTO for the U.S. Appl. No. 14/239,997, dated Nov. 16, 2016.
International Preliminary Report on Patentability (Chapter I) for PCT/IL2013/050806, dated Mar. 31, 2015.
Non-Final Rejection Office Action issued by the USPTO for the U.S. Appl. No. 14/813,170, dated Dec. 9, 2016.
Non-Final Rejection Office Action issued by the USPTO for the U.S. Appl. No. 12/441,838, dated Aug. 16, 2013.
International Preliminary Report on Patentability (Chapter I) for PCT/IL2012/000342, dated Mar. 25, 2014.
Restriction Requirement Office Action issued by the USPTO for the U.S. Appl. No. 14/239,997, dated May 16, 2016.
Restriction Requirement Office Action issued by the USPTO for the U.S. Appl. No. 14/154,225, dated Sep. 24, 2015.

(56) References Cited

OTHER PUBLICATIONS

Restriction Requirement Office Action issued by the USPTO for the U.S. Appl. No. 14/380,082, dated Sep. 26, 2016.
Restriction Requirement Office Action issued by the USPTO for the U.S. Appl. No. 12/667,420, dated Nov. 27, 2012.
Restriction Requirement Office Action issued by the USPTO for the U.S. Appl. No. 13/265,206, dated Dec. 2, 2013.
Extended European Search Report issued by the EPO for the European Application No. 14151130.3, dated Apr. 1, 2014.
Extended European Search Report issued by the EPO for the European Application No. 10766746.1, dated Jan. 17, 2014.
Extended European Search Report issued by the EPO for the European Application No. 140150541.2, dated Aug. 22, 2014.
International Preliminary Report on Patentability (Chapter I) for PCT/IL2008/000902, dated Jan. 5, 2010.
International Preliminary Report on Patentability (Chapter I) for PCT/IL2015/050718, dated Jan. 10, 2017.
International Preliminary Report on Patentability (Chapter I) for PCT/IL2012/000310, dated Feb. 25, 2014.
International Preliminary Report on Patentability (Chapter I) for PCT/IL2012/000312, dated Feb. 25, 2014.
Response dated Dec. 28, 2012, to Restriction Requirement Office Action issued by the USPTO for the U.S. Appl. No. 12/667,420, dated Nov. 27, 2012.
Final Rejection Office Action issued for U.S. Appl. No. 14/816,127 dated Aug. 11, 2017.
Response dated Nov. 19, 2013, to Non-Final Rejection Office Action issued by the USPTO for the U.S. Appl. No. 12/441,838, dated Nov. 12, 2013.
Response dated May 25, 2016, to Non-Final Rejection Office Action issued by the USPTO for the U.S. Appl. No. 14/154,225, dated Jan. 11, 2016.
Written Opinion of International Search Authority for PCT/IL2012/000312, dated Jan. 8, 2013.
Written Opinion of International Search Authority for PCT/IL2013/050806, dated Feb. 10, 2014.
Written Opinion of International Search Authority for PCT/IL2012/000311, dated Feb. 13, 2013.
Written Opinion of International Search Authority for PCT/IL2012/000342, dated Feb. 25, 2013.
Written Opinion of International Search Authority for PCT/IL2012/000310, dated Feb. 28, 2013.
Written Opinion of International Search Authority for PCT/IL2008/000902, dated Mar. 2, 2009.
Written Opinion of International Search Authority for PCT/IL2014/050022, dated May 12, 2014.
Written Opinion of International Search Authority for PCT/IL2013/050183, dated Jun. 28, 2013.
Written Opinion of International Search Authority for PCT/IL2010/000330, dated Aug. 10, 2010.
Written Opinion of International Search Authority for PCT/IL2013/050216, dated Aug. 20, 2013.
Written Opinion of International Search Authority for PCT/IL2015/050345, dated Sep. 2, 2015.
Written Opinion of International Search Authority for PCT/IL2006/000478, dated Sep. 5, 2007.
Written Opinion of International Search Authority for PCT/IL2007/001161, dated Sep. 12, 2008.
Written Opinion of International Search Authority for PCT/IL2015/050579, dated Nov. 2, 2015.
Written Opinion of International Search Authority for PCT/IL2015/050349, dated Nov. 4, 2015.
Written Opinion of International Search Authority for PCT/IL2015/050718, dated Nov. 10, 2015.
Written Opinion of International Search Authority for PCT/IL2008/000994, dated Dec. 1, 2008.
Response to Non-Final Rejection Office Action issued for U.S. Appl. No. 14/817,245 dated Feb. 8, 2017, dated Aug. 6, 2017.
Final Rejection Office Action issued for U.S. Appl. No. 14/817,245 dated Sep. 11, 2017.
Corresponding U.S. Appl. No. 15/322,452, filed Dec. 28, 2016 (not published yet).
Corresponding U.S. Appl. No. 15/393,286, filed Dec. 29, 2016 (not published yet).
Non-Final Rejection Office Action issued for U.S. Appl. No. 13/223,767, dated Jun. 14, 2012.
Response to Non-Final Rejection Office Action issued for U.S. Appl. No. 13/223,767, dated Jun. 14, 2012, dated Sep. 13, 2012.
Requirement for Restriction/Election Office Action issued for U.S. Appl. No. 11/874,576, dated Dec. 31, 2009.
Response to Requirement for Restriction/Election Office Action issued for U.S. Appl. No. 11/874,576, dated Dec. 31, 2009, dated Feb. 26, 2010.
Non-Final Rejection Office Action issued for U.S. Appl. No. 11/874,576, dated Apr. 19, 2010.
Response to Non-Final Rejection Office Action issued for U.S. Appl. No. 11/874,576, dated Apr. 19, 2010, dated Oct. 19, 2010.
Final Rejection Office Action issued for U.S. Appl. No. 11/874,576, dated Jan. 4, 2011.
Response to Final Rejection Office Action issued for U.S. Appl. No. 11/874,576, dated Jan. 4, 2011, dated Apr. 4, 2011.
Non-Final Rejection Office Action issued for U.S. Appl. No. 11/874,576, dated Apr. 13, 2012.
Response to Non-Final Rejection Office Action issued for U.S. Appl. No. 11/874,576, dated Apr. 13, 2012, dated May 3, 2012.
Requirement for Restriction/Election Office Action issued for U.S. Appl. No. 11/874,534, dated Aug. 17, 2012.
Response to Requirement for Restriction/Election Office Action issued for U.S. Appl. No. 11/874,534, dated Aug. 17, 2012, dated Dec. 16, 2012.
Written Opinion of International Search Authority for PCT/IL2012/000309, dated Feb. 7, 2013.
International Preliminary Report on Patentability (Chapter I) for PCT/IL2012/000309, dated Feb. 25, 2014.
Response to Requirement for Restriction/Election Office Action issued for U.S. Appl. No. 14/380,082, dated Sep. 26, 2016, dated Mar. 22, 2017.
Response to Non-Final Rejection Office Action issued for U.S. Appl. No. 14/239,897 dated Oct. 7, 2016, dated Mar. 23, 2017.
Non-Final Rejection Office Action issued for U.S. Appl. No. 11/874,576, dated Apr. 26, 2016.
Final Rejection Office Action issued for U.S. Appl. No. 14/239,997, dated Aug. 18, 2017.
Response to Non-Final Rejection Office Action issued for U.S. Appl. No. 14/239,997 dated Nov. 16, 2016, dated May 15, 2017.
Response to Non-Final Rejection Office Action issued for U.S. Appl. No. 14/813,179 dated Dec. 9, 2016, dated Jun. 5, 2017.
Final Rejection Office Action issued for U.S. Appl. No. 14/816,099, dated Aug. 9, 2017.
Response to Non-Final Rejection Office Action issued for U.S. Appl. No. 14/816,099 dated Jan. 26, 2017, dated Jul. 24, 2017.
Response to Non-Final Rejection Office Action issued for U.S. Appl. No. 14/816,127 dated Jan. 26, 2017, dated Jul. 24, 2017.
Final Rejection Office Action issued for U.S. Appl. No. 15/169,990 dated Sep. 14, 2017.
Response to Non-Final Rejection Office Action issued for U.S. Appl. No. 15/169,990 dated Feb. 24, 2017, dated Aug. 15, 2017.
Non-Final Rejection Office Action issued for U.S. Appl. No. 14/239,897 dated Aug. 23, 2017.
Response to Final Rejection Office Action issued for U.S. Appl. No. 15/086,194 dated Feb. 27, 2017, dated Aug. 17, 2017.
Response to Ex Parte Quayle Action issued for U.S. Appl. No. 13/265,206 dated Mar. 14, 2017, dated Aug. 9, 2017.
Requirement for Restriction/Election Office Action issued for U.S. Appl. No. 14/650,315 dated Jul. 31, 2017.

* cited by examiner

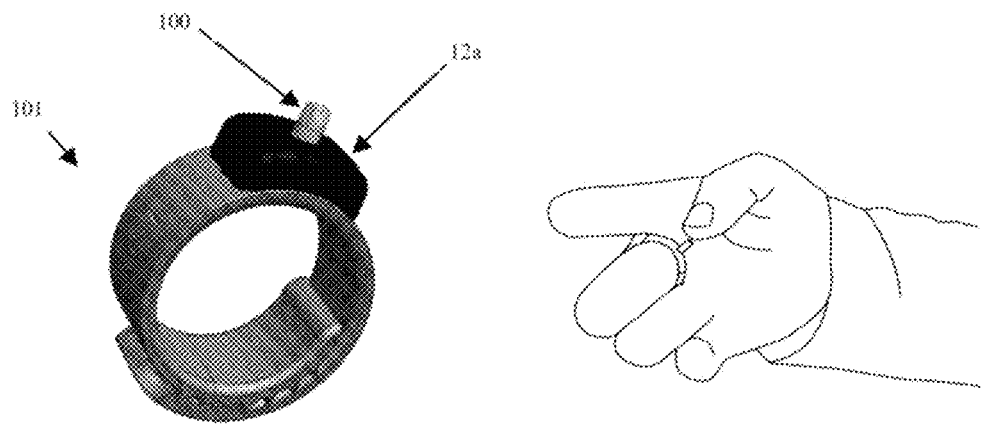
*Fig. 7a*          *Fig. 7b*
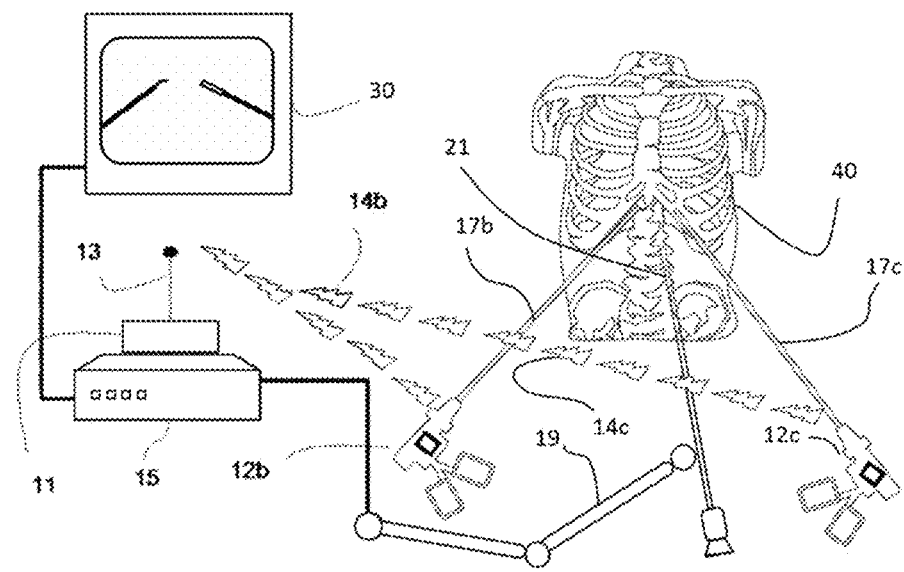
*Fig. 8*

DEVICE HAVING A WEARABLE INTERFACE FOR IMPROVING LAPAROSCOPIC SURGERY AND METHODS FOR USE THEREOF

FIELD OF THE INVENTION

The present invention generally relates to means and methods for improving the interface between the surgeon and the operating medical assistant or between the surgeon and an endoscope system for laparoscopic surgery. Moreover, this present invention discloses a device useful for controlling an endoscope system for laparoscopic surgery comprising a wearable interface for enhancing the control of an endoscope system during laparoscopic surgery.

BACKGROUND OF THE INVENTION

In laparoscopic surgery, the surgeon performs the operation through small holes using long instruments and observing the internal anatomy with an endoscope camera. The endoscope is conventionally held by a camera human assistant (i.e. operating medical assistant) since the surgeon must perform the operation using both hands. The surgeon performance is largely dependent on the camera position relative to the instruments and on a stable image shown at the monitor. The main problem is that it is difficult for the operating medical assistant to hold the endoscope steady, keeping the scene upright.

Laparoscopic surgery is becoming increasingly popular with patients because the scars are smaller and their period of recovery is shorter. Laparoscopic surgery requires special training of the surgeon or gynecologist and the theatre nursing staff. The equipment is often expensive and not available in all hospitals.

During laparoscopic surgery it is often required to shift the spatial placement of the endoscope in order to present the surgeon with an optimal view. Conventional laparoscopic surgery makes use of either human assistants that manually shift the instrumentation or, alternatively, robotic automated assistants. Automated assistants utilize interfaces that enable the surgeon to direct the mechanical movement of the assistant, achieving a shift in the camera view.

U.S. Pat. No. 6,714,841 discloses an automated camera endoscope in which the surgeon is fitted with a head mounted light source that transmits the head movements to a sensor, forming an interface that converts the movements to directions for the mechanical movement of the automated assistant. Alternative automated assistants incorporate a voice operated interface, a directional key interface, or other navigational interfaces. The above interfaces share the following drawbacks:

a. A single directional interface that provide limited feedback to the surgeon
b. A cumbersome serial operation for starting and stopping movement directions that requires the surgeon's constant attention, preventing the surgeon from keeping the flow of the surgical procedure.

Research has suggested that these systems divert the surgeons focus from the major task at hand. Therefore technologies assisted by magnets and image processing have been developed to simplify interfacing control. However, these improved technologies still fail to address another complicating interface aspect of laparoscopic surgery, in that they do not allow the surgeon to signal to automated assistants, to human assistants or to surgical colleagues which instrument his attention is focused on.

Hence there is still a long felt need for improving the interface between the surgeon, his surgical colleagues or human assistants and an endoscope system, for laparoscopic surgery.

SUMMARY OF THE INVENTION

It is one object of the present invention to disclose a device useful for the surgeon and the automated assistant interface, and/or the surgeon and the operating medical assistant interface, during laparoscopic surgery; wherein the device is adapted to control and/or direct the automated endoscope assistant to focus the endoscope on the desired instrument of the surgeon; further wherein the device is adapted to focus the operating medical assistant on the desired instrument of the surgeon.

It is another object of the present invention to disclose the device as defined above, wherein said device additionally comprising:

a. at least one wireless transmitter with at least one operating key;
b. at least one wireless receiver;
c. at least one conventional laparoscopy computerized system; said conventional laparoscopy computerized system is adapted to load a surgical instrument spatial locating software, and an automated assistant maneuvering software; said locating software enables a visual response to the depression of said at least one key on said wireless transmitter; said maneuvering software enables the movement of said endoscope; and
d. at least one video screen.

It is another object of the present invention to disclose the device as defined above, wherein each said instrument is fitted with a wireless transmitter.

It is another object of the present invention to disclose the device as defined above, wherein said wireless transmitter is freestanding.

It is another object of the present invention to disclose the device as defined above, wherein said wireless transmitter is adapted to locate the position of each instrument.

It is another object of the present invention to disclose the device as defined above, wherein said selection of said desired instrument is confirmed by clicking on said at least one key.

It is another object of the present invention to disclose the device as defined above, wherein said selection of said desired instrument is confirmed by depression of said at least one key on said wireless transmitter.

It is another object of the present invention to disclose the device as defined above, wherein said depression of said at least one key is a prolonged depression.

It is another object of the present invention to disclose a method useful for surgeon and the automated assistant interface, and/or said surgeon and the operating medical assistant interface, during laparoscopic surgery. The method comprises step selected inter alia from (a) obtaining a device as defined above; (b) selecting said desired instrument; and (c) displaying said desired instrument on a screen; wherein said device controlling and/or directing said automated endoscope assistant and thereby focusing said endoscope on said desired instrument of said surgeon.

It is another object of the present invention to disclose the method as defined above, additionally comprising the step of confirming by the selection of said desired instrument.

It is another object of the present invention to disclose the method as defined above, additionally comprising the step of extracting said desired instrument form said screen.

It is another object of the present invention to disclose the method as defined above, additionally comprising the step of instructing said automated assistant to focus said endoscope on said desired instrument.

It is another object of the present invention to disclose the method as defined above, wherein said step of selecting said desired instrument additionally comprising the steps of (a) depressing of said at least one key on said wireless transmitter; (b) transmitting a generic code to said receiver; (c) communicating said signal to the computer.

It is another object of the present invention to disclose the method as defined above, wherein said step of selecting said desired instrument additionally comprising the step confirming the selection of said desired instrument by clicking on said at least one key.

It is another object of the present invention to disclose the method as defined above, wherein said step of selecting said desired instrument additionally comprising the step confirming the selection of said desired instrument by a prolonged depression on said at least one key.

It is another object of the present invention to disclose the method as defined above, additionally comprising the step of re-selecting said desired instrument until said desired instrument is selected.

It is another object of the present invention to disclose the method as defined above, additionally comprising the step of identifying each of said instruments to said computerized system.

It is another object of the present invention to disclose the method as defined above, additionally comprising the step of attaching said wireless transmitter to said surgical instrument.

It is another object of the present invention to disclose the method as defined above, additionally comprising the step of matching each transmitted code from said depressed wireless transmitter to said surgical instrument.

It is another object of the present invention to disclose the method as defined above, wherein said step of matching each transmitted code additionally comprising the step of storing said matching database on a computer.

It is another object of the present invention to disclose the method as defined above, additionally comprising the step of signing said surgical instrument by a temporary onscreen graphic symbol and presenting upon the onscreen depiction of the surgical instrument.

It is another object of the present invention to disclose the method as defined above, additionally comprising the step of continuously displaying said selection graphic symbol.

It is another object of the present invention to disclose the method as defined above, wherein the selection of the surgical instrument is signified by a continuous onscreen graphic symbol presented upon the onscreen depiction of the surgical instrument.

It is another an object of the present invention to disclose the method as defined above, additionally comprising the step of calculating the position of each said instrument.

It is another object of the present invention to provide a device useful for the interface between a surgeon and an automated assistant, comprising:
  a. at least one endoscope, mechanically interconnected to said automated assistant; said automated assistant is adapted to maneuver said endoscope to a desired location;
  b. at least one instrument;
  c. at least one wearable operator comprising at least one wireless transmitter, adapted to transmit a signal once said at least one wearable operator is activated; said at least one wearable operator is in communication with said at least one of said instrument;
  d. at least one wireless receiver; adapted to receive said signal sent by said transmitter;
  e. at least one laparoscopy computerized system, in communication with said wireless receiver, adapted to provide a visual onscreen depiction of said at least one instrument to be selected following the activation of said at least one wearable operator; and,
  f. at least one video screen;
  wherein said device is adapted to control and to direct said endoscope via said laparoscopy computerized system and said automated assistant on said instrument to be selected following the activation of said at least one wearable operator.

It is another object of the present invention to provide the device as defined above, wherein at least one of said wearable operators is either wire or wirelessly coupled to said at least one of said instruments.

It is another object of the present invention to provide the device as defined above, wherein said device is adapted to control and to direct said endoscope via said laparoscopy computerized system and said automated assistant on said instrument to which said activated wearable operator is coupled.

It is another object of the present invention to provide the device as defined above, wherein said wearable operator is worn by said surgeon on a predetermined body part.

It is another object of the present invention to provide the device as defined above, wherein said predetermined body part is selected from a group consisting of the hand of said surgeon, at least one of the fingers of said surgeon, the thigh of said surgeon, the neck of said surgeon, at least one of the legs of said surgeon, the knee of said surgeon, the head of said surgeon and any combination thereof.

It is another object of the present invention to provide the device as defined above, wherein the shape of said wearable operator is selected from a group consisting of a ring, a bracelet and any combination thereof.

It is another object of the present invention to provide the device as defined above, wherein said wearable operator is coupled to a predetermined location on said instrument by means of an adaptor.

It is another object of the present invention to provide the device as defined above, wherein said wearable operator is adjustable so as to fit said predetermined location of said different instruments, each of which is characterized by a different size and shape.

It is another object of the present invention to provide the device as defined above, wherein said wearable operator comprises a body having at least two portions at least partially overlapping each other; said two portions are adapted to grasp and hold either said instrument or said predetermined body part there-between, such that a tight-fit coupling between said two portions and said instrument or said predetermined body part is obtained.

It is another object of the present invention to provide the device as defined above, wherein one of said two portions is rotationally movable relative to the other, such that when said wearable operator is coupled to said instrument, fine-tuned movement of said two body portions is obtainable so as to provide said tight-fit coupling between said two portions and said instrument or said predetermined body part.

It is another object of the present invention to provide the device as defined above, wherein said two portions are rotationally movable relative to each other, such that when said wearable operator is coupled to said instrument, fine-tuned movement of said two body portions is obtainable so as to provide said tight-fit coupling between said two portions and said instrument or said predetermined body part.

It is another object of the present invention to provide the device as defined above, wherein said wearable operator comprises (a) at least one flexible and stretchable strip; and, (b) loop-closing means adapted to close a loop with said at least one flexible and stretchable strip; said at least one flexible and stretchable strip and said loop-closing means are provided so as to fit said wearable operator to at least one selected from a group consisting of (a) said predetermined location of said different instruments; (b) said predetermined body part of said surgeon, each of which is characterized by a different size and shape.

It is another object of the present invention to provide the device as defined above, wherein said flexible and stretchable strip is made of material selected from a group consisting of silicone, rubber and any combination thereof.

It is another object of the present invention to provide the device as defined above, wherein said loop-closing means is at least one unidirectional catch through which said flexible and stretchable strip is passed so as to provide a loop.

It is another object of the present invention to provide the device as defined above, wherein said loop-closing means is at least one peg around which said flexible and stretchable strip is passed so as to provide a loop.

It is another object of the present invention to provide the device as defined above, wherein said flexible and stretchable strip is characterized by a varied width along its length.

It is another object of the present invention to provide the device as defined above, wherein said flexible and stretchable strip is characterized by different surface roughnesses along its length.

It is another object of the present invention to provide the device as defined above, wherein said wireless transmitter is freestanding.

It is another object of the present invention to provide the device as defined above, wherein each of said at least one instrument is fitted with at least one of said wireless transmitters.

It is another object of the present invention to provide the device as defined above, wherein said wireless transmitter is adapted to locate the position of at least one of said instruments.

It is another object of the present invention to provide the device as defined above, wherein a selection of said at least one instrument is obtained by clicking on said at least one wearable operator.

It is another object of the present invention to provide the device as defined above, wherein the activation of said at least one wearable operator is obtained by depression on the same, voice activating the same, prolonged depression on the same, double clicking on the same and any combination thereof.

It is another object of the present invention to provide the device as defined above, wherein said laparoscopy computerized system directs said endoscope by using image information shown on said video screen without said help of assistants.

It is another object of the present invention to provide the device as defined above, wherein said conventional laparoscopy computerized system comprises at least one surgical instrument spatial location software, adapted to locate the 3D spatial position of said at least one instrument.

It is another object of the present invention to provide the device as defined above, wherein said conventional laparoscopy computerized system comprises at least one automated assistant maneuvering system; said automated assistant maneuvering system is coupled to said endoscope and is adapted to direct said endoscope to said at least one instrument, said instrument selected following the activation of said at least one wearable operator.

It is another object of the present invention to provide the device as defined above, wherein each transmitted signal from said wearable operator and said wireless transmitter is matched to at least one of said instruments.

It is another object of the present invention to provide a surgical system comprising:
 a. at least one laparoscopic instrument;
 b. at least one wearable operator comprising at least one wireless transmitter capable of being activated to transmit a signal;
 c. at least one computerized platform configured for tracking said at least one laparoscopic instrument and being capable of receiving said signal and identifying to a user a laparoscopic instrument selected by activation of said transmitter from said at least one laparoscopic instrument; wherein said wearable operator is being worn by the surgeon.

It is another object of the present invention to provide the system as defined above, wherein said wearable operator is activated manually or automatically.

It is another object of the present invention to provide the system as defined above, wherein said computerized platform tracks said laparoscopic instrument selected upon activation of said transmitter.

It is another object of the present invention to provide the system as defined above, wherein said wireless transmitter is freestanding.

It is another object of the present invention to provide the system as defined above, wherein said at least one wireless transmitter is attached to said at least one laparoscopic instrument.

It is another object of the present invention to provide the system as defined above, wherein said identifying to said user of said laparoscopic instrument is effected via a visual depiction of said laparoscopic instrument on a display.

It is another object of the present invention to provide the system as defined above, further comprising an automated assistant for controlling an endoscopic camera.

It is another object of the present invention to provide the system as defined above, wherein said computerized platform tracks said laparoscopic instrument using image information received from said endoscopic camera.

It is another object of the present invention to provide the system as defined above, wherein said computerized platform controls said automated assistant.

It is another object of the present invention to provide the system as defined above, wherein said computerized platform visually identifies said laparoscopic instrument to said user upon activation of said transmitter.

It is another object of the present invention to provide the system as defined above, wherein at least one of said wearable operators is either wire or wirelessly coupled to said at least one of said laparoscopic instruments.

It is another object of the present invention to provide the system as defined above, wherein said computerized platform is adapted to track and to identify said laparoscopic instrument to which said wearable operator is coupled.

It is another object of the present invention to provide the system as defined above, wherein said wearable operator is worn by said surgeon on a predetermined body part.

It is another object of the present invention to provide the system as defined above, wherein said predetermined body part is selected from a group consisting of the hand of said surgeon, at least one of the fingers of said surgeon, the thigh of said surgeon, the neck of said surgeon, at least one of the legs of said surgeon, the knee of said surgeon, the head of said surgeon and any combination thereof.

It is another object of the present invention to provide the system as defined above, wherein the shape of said wearable operator is selected from a group consisting of a ring, a bracelet and any combination thereof.

It is another object of the present invention to provide the system as defined above, wherein said wearable operator is coupled to a predetermined location on said instrument by means of an adaptor.

It is another object of the present invention to provide the system as defined above, wherein said wearable operator is adjustable so as to fit said predetermined location of said different instruments, each of which is characterized by a different size and shape.

It is another object of the present invention to provide the system as defined above, wherein said wearable operator comprises a body having at least two portions at least partially overlapping each other; said two portions are adapted to grasp and hold either said instrument or said predetermined body part there-between, such that a tight-fit coupling between said two portions and said instrument or said predetermined body part is obtained.

It is another object of the present invention to provide the system as defined above, wherein one of said two portions is rotationally movable relative to the other, such that when said wearable operator is coupled to said instrument, fine-tuned movement of said two body portions is obtainable so as to provide said tight-fit coupling between said two portions and said instrument or said predetermined body part.

It is another object of the present invention to provide the system as defined above, wherein said two portions are rotationally movable relative to each other, such that when said wearable operator is coupled to said instrument, fine-tuned movement of said two body portions is obtainable so as to provide said tight-fit coupling between said two portions and said instrument or said predetermined body part.

It is another object of the present invention to provide the system as defined above, wherein said wearable operator comprises (a) at least one flexible and stretchable strip; and, (b) loop-closing means adapted to close a loop with said at least one flexible and stretchable strip; said at least one flexible and stretchable strip and said loop-closing means are provided so as to fit said wearable operator to at least one selected from a group consisting of (a) said predetermined location of said different instruments; (b) said predetermined body part of said surgeon, each of which is characterized by a different size and shape.

It is another object of the present invention to provide the system as defined above, wherein said flexible and stretchable strip is made of material selected from a group consisting of silicone, rubber and any combination thereof.

It is another object of the present invention to provide the system as defined above, wherein said loop-closing means is at least one unidirectional catch through which said flexible and stretchable strip is passed so as to provide a loop.

It is another object of the present invention to provide the system as defined above, wherein said loop-closing means is at least one peg around which said flexible and stretchable strip is passed so as to provide a loop.

It is another object of the present invention to provide the system as defined above, wherein said flexible and stretchable strip is characterized by a varied width along its length.

It is another object of the present invention to provide the system as defined above, wherein said flexible and stretchable strip is characterized by different surface roughnesses along its length.

It is another object of the present invention to provide the system as defined above, wherein said wireless transmitter is freestanding.

It is another object of the present invention to provide the system as defined above, wherein each of said at least one laparoscopic instruments is fitted with at least one of said wireless transmitters.

It is another object of the present invention to provide the system as defined above, wherein said wireless transmitter is adapted to locate the position of at least one of said laparoscopic instruments.

It is another object of the present invention to provide the system as defined above, wherein selection of said at least one laparoscopic instrument is confirmed by activating said at least one wearable operator It is another object of the present invention to provide the system as defined above, wherein the activation of said at least one wearable operator is obtained by depression on the same, voice activating the same, prolonged depression on the same, double clicking on the same and any combination thereof.

It is another object of the present invention to provide the system as defined above, wherein said computerized platform directs an endoscope to said laparoscopic instrument by using image information shown on a video screen without said help of assistants.

It is another object of the present invention to provide the system as defined above, wherein each transmitted signal from said wearable operator and said wireless transmitter is matched to at least one of said instruments.

It is another object of the present invention to provide a method useful for the interface between a surgeon and an automated assistant; said method comprising the step of:
a. obtaining a device comprising:
  i. at least one desired laparoscopic instrument;
  ii. at least one endoscope, mechanically interconnected to said automated assistant;
  iii. at least one wearable operator comprising at least one wireless transmitter;
  iv. at least one wireless receiver;
  v. at least one laparoscopy computerized system loaded with (i) surgical instrument spatial location software; (ii) automated assistant maneuvering software; (iii) and, a software that enables a visual onscreen depiction response to the activation of said at least one wearable operator; and,
  vi. at least one video screen;
b. activating said wearable operator; thereby selecting a desired laparoscopic instrument and emitting a signal;
c. receiving said signal by said receiver;
d. maneuvering said endoscope so as to focus said endoscope on said desired laparoscopic instrument of said surgeon; and,
e. displaying said desired instrument on a screen;
wherein said device is adapted to control and to direct said endoscope via said laparoscopy computerized system and said automated assistant on said instrument to be selected following the activation of said at least one wearable operator.

It is another object of the present invention to provide the method as defined above, additionally comprising the step of manually or automatically activating said wearable operator.

It is another object of the present invention to provide the method as defined above, wherein said wireless transmitter is freestanding.

It is another object of the present invention to provide the method as defined above, additionally comprising the step of attaching said at least one wireless transmitter to said at least one desired laparoscopic instrument.

It is another object of the present invention to provide the method as defined above, additionally comprising the step of identifying to said user of said desired laparoscopic instrument; further wherein said step is effected via a visual depiction of said laparoscopic instrument on a display.

It is another object of the present invention to provide the method as defined above, wherein said laparoscopy computerized system tracks said laparoscopic instrument using image information received from said endoscopic camera.

It is another object of the present invention to provide the method as defined above, wherein said laparoscopy computerized system controls said automated assistant.

It is another object of the present invention to provide the method as defined above, wherein said laparoscopy computerized system visually identifies said laparoscopic instrument to said user upon activation of said transmitter.

It is another object of the present invention to provide the method as defined above, additionally comprising step of confirming the selection of said desired instrument.

It is another object of the present invention to provide the method as defined above, wherein said step of selecting said desired laparoscopic instrument additionally comprises the steps of (a) activating wearable operator; (b) transmitting a generic code to said receiver; (c) communicating said signal to a computer, thereby operating said automated assistant.

It is another object of the present invention to provide the method as defined above, wherein said step of selecting said desired laparoscopic instrument additionally comprises the step of confirming the selection of said desired laparoscopic instrument by clicking on said wearable operator.

It is another object of the present invention to provide the method as defined above, wherein said step of selecting said desired laparoscopic instrument additionally comprises the step confirming the selection of said laparoscopic desired instrument by a prolonged depression on said wearable operator.

It is another object of the present invention to provide the method as defined above, additionally comprising the step of identifying each of said desired laparoscopic instrument to said computerized system.

It is another object of the present invention to provide the method as defined above, additionally comprising the step of attaching said wearable operator to said laparoscopic instrument.

It is another object of the present invention to provide the method as defined above, additionally comprising the step of matching each transmitted code from said wearable operator and said wireless transmitter to at least one of said laparoscopic instruments.

It is another object of the present invention to provide the method as defined above, additionally comprising step of either wire or wirelessly coupling at least one of said wearable operators to said at least one of said instruments.

It is another object of the present invention to provide the method as defined above, additionally comprising step of controlling and directing said endoscope via said laparoscopy computerized system and said automated assistant on said desired laparoscopic instrument to which said activated wearable operator is coupled.

It is another object of the present invention to provide the method as defined above, additionally comprising step of wearing said wearable operator by said surgeon on a predetermined body part.

It is another object of the present invention to provide the method as defined above, additionally comprising step of selecting said predetermined body part from a group consisting of the hand of said surgeon, at least one of the fingers of said surgeon, the thigh of said surgeon, the neck of said surgeon, at least one of the legs of said surgeon, the knee of said surgeon, the head of said surgeon and any combination thereof.

It is another object of the present invention to provide the method as defined above, additionally comprising step of selecting the shape of said wearable operator from a group consisting of a ring, a bracelet and any combination thereof.

It is another object of the present invention to provide the method as defined above, additionally comprising step of coupling said wearable operator to a predetermined location on said instrument by means of an adaptor.

It is another object of the present invention to provide the method as defined above, additionally comprising step of adjusting said wearable operator so as to fit said predetermined location of said different instruments, each of which is characterized by a different size and shape.

It is another object of the present invention to provide the method as defined above, additionally comprising step of providing said wearable operator with a body having at least two portions at least partially overlapping each other; said two portions are adapted to grasp and hold either said instrument or said predetermined body part there-between, such that a tight-fit coupling between said two portions and said instrument or said predetermined body part is obtained.

It is another object of the present invention to provide the method as defined above, wherein one of said two portions is rotationally movable relative to the other, such that when said wearable operator is coupled to said instrument, fine-tuned movement of said two body portions is obtainable so as to provide said tight-fit coupling between said two portions and said instrument or said predetermined body part.

It is another object of the present invention to provide the method as defined above, additionally comprising step of coupling wherein said two portions are rotationally movable relative to each other, such that when said wearable operator is coupled to said instrument, fine-tuned movement of said two body portions is obtainable so as to provide said tight-fit coupling between said two portions and said instrument or said predetermined body part.

It is another object of the present invention to provide the method as defined above, wherein said wearable operator comprises (a) at least one flexible and stretchable strip; and, (b) loop-closing means adapted to close a loop with said at least one flexible and stretchable strip; said at least one flexible and stretchable strip and said loop-closing means are provided so as to fit said wearable operator to at least one selected from a group consisting of (a) said predetermined location of said different instruments; (b) said predetermined body part of said surgeon, each of which is characterized by a different size and shape.

It is another object of the present invention to provide the method as defined above, additionally comprising step of providing said flexible and stretchable strip to be made of material selected from a group consisting of silicone, rubber and any combination thereof.

It is another object of the present invention to provide the method as defined above, wherein said loop-closing means is at least one unidirectional catch through which said flexible and stretchable strip is passed so as to provide a loop.

It is another object of the present invention to provide the method as defined above, wherein said loop-closing means is at least one peg around which said flexible and stretchable strip is passed so as to provide a loop.

It is another object of the present invention to provide the method as defined above, wherein said flexible and stretchable strip is characterized by a varied width along its length.

It is another object of the present invention to provide the method as defined above, wherein said flexible and stretchable strip is characterized by different surface roughnesses along its length.

It is another object of the present invention to provide the method as defined above, wherein said wireless transmitter is freestanding.

It is another object of the present invention to provide the method as defined above, wherein each of said at least one instrument is fitted with at least one of said wireless transmitters.

It is another object of the present invention to provide the method as defined above, wherein said wireless transmitter is adapted to locate the position of at least one of said instruments.

It is another object of the present invention to provide the method as defined above, additionally comprising step of selecting said at least one instrument by activating said at least one wearable operator.

It is another object of the present invention to provide the method as defined above, additionally comprising step of activating said at least one wearable operator by depression on the same, voice activating the same, prolonged depression on the same, double clicking on the same and any combination thereof.

It is another object of the present invention to provide a method useful for the interface between a surgeon and an automated assistant; said method comprising the step of:
  a. obtaining a surgical system comprising:
    i. at least one laparoscopic instrument;
    ii. at least one wearable operator comprising at least one wireless transmitter capable of being activated to transmit a signal;
    iii. at least one a computerized platform configured for tracking said at least one laparoscopic instrument and being capable of receiving said signal and identifying to a user a laparoscopic instrument selected by activation of said transmitter from said at least one laparoscopic instrument; wherein said wearable operator is being worn by the surgeon;
  b. activating said wearable operator; thereby selecting a desired laparoscopic instrument and emitting a signal;
  c. receiving said signal by said receiver;
  d. maneuvering an endoscope so as to focus the same on said desired laparoscopic instrument of said surgeon; and,
  e. displaying said desired instrument on a screen;
  wherein said system is adapted to control and to direct said endoscope via said laparoscopy computerized system and said automated assistant on said instrument to be selected following the activation of said at least one wearable operator.

It is another object of the present invention to provide the method as defined above, additionally comprising step of manually or automatically activating said wearable operator.

It is another object of the present invention to provide the method as defined above, additionally comprising step of tracking said laparoscopic instrument selected upon activation of said transmitter by means of said computerized platform.

It is another object of the present invention to provide the method as defined above, wherein said wireless transmitter is freestanding.

It is another object of the present invention to provide the method as defined above, additionally comprising step of attaching said at least one wireless transmitter to said at least one laparoscopic instrument.

It is another object of the present invention to provide the method as defined above, additionally comprising step of identifying to said user of said laparoscopic instrument via a visual depiction of said laparoscopic instrument on a display.

It is another object of the present invention to provide the method as defined above, additionally comprising step of providing an automated assistant for controlling an endoscopic camera.

It is another object of the present invention to provide the method as defined above, wherein said computerized platform tracks said laparoscopic instrument using image information received from said endoscopic camera.

It is another object of the present invention to provide the method as defined above, additionally comprising step of controlling said automated assistant by means of said computerized platform.

It is another object of the present invention to provide the method as defined above, wherein said computerized platform visually identifies said laparoscopic instrument to said user upon activation of said transmitter.

It is another object of the present invention to provide the method as defined above, wherein at least one of said wearable operators is either wire or wirelessly coupled to said at least one of said laparoscopic instruments.

It is another object of the present invention to provide the method as defined above, wherein said computerized platform is adapted to track and to identify said laparoscopic instrument to which said wearable operator is coupled.

It is another object of the present invention to provide the method as defined above, additionally comprising step of wearing said wearable operator by said surgeon on a predetermined body part.

It is another object of the present invention to provide the method as defined above, wherein said predetermined body part is selected from a group consisting of the hand of said surgeon, at least one of the fingers of said surgeon, the thigh of said surgeon, the neck of said surgeon, at least one of the legs of said surgeon, the knee of said surgeon, the head of said surgeon and any combination thereof.

It is another object of the present invention to provide the method as defined above, wherein the shape of said wearable operator is selected from a group consisting of a ring, a bracelet and any combination thereof.

It is another object of the present invention to provide the method as defined above, additionally comprising step of coupling said wearable operator to a predetermined location on said instrument by means of an adaptor.

It is another object of the present invention to provide the method as defined above, wherein said wearable operator is adjustable so as to fit said predetermined location of said different instruments, each of which is characterized by a different size and shape.

It is another object of the present invention to provide the method as defined above, additionally comprising step of providing said wearable operator with a body having at least two portions at least partially overlapping each other; said two portions are adapted to grasp and hold either said instrument or said predetermined body part there-between, such that a tight-fit coupling between said two portions and said instrument or said predetermined body part is obtained.

It is another object of the present invention to provide the method as defined above, wherein one of said two portions is rotationally movable relative to the other, such that when said wearable operator is coupled to said instrument, fine-tuned movement of said two body portions is obtainable so as to provide said tight-fit coupling between said two portions and said instrument or said predetermined body part.

It is another object of the present invention to provide the method as defined above, wherein said two portions are rotationally movable relative to each other, such that when said wearable operator is coupled to said instrument, fine-tuned movement of said two body portions is obtainable so as to provide said tight-fit coupling between said two portions and said instrument or said predetermined body part.

It is another object of the present invention to provide the method as defined above, wherein said wearable operator comprises (a) at least one flexible and stretchable strip; and, (b) loop-closing means adapted to close a loop with said at least one flexible and stretchable strip; said at least one flexible and stretchable strip and said loop-closing means are provided so as to fit said wearable operator to at least one selected from a group consisting of (a) said predetermined location of said different instruments; (b) said predetermined body part of said surgeon, each of which is characterized by a different size and shape.

It is another object of the present invention to provide the method as defined above, wherein said flexible and stretchable strip is made of material selected from a group consisting of silicone, rubber and any combination thereof.

It is another object of the present invention to provide the method as defined above, wherein said loop-closing means is at least one unidirectional catch through which said flexible and stretchable strip is passed so as to provide a loop.

It is another object of the present invention to provide the method as defined above, wherein said loop-closing means is at least one peg around which said flexible and stretchable strip is passed so as to provide a loop.

It is another object of the present invention to provide the method as defined above, wherein said flexible and stretchable strip is characterized by a varied width along its length.

It is another object of the present invention to provide the method as defined above, wherein said flexible and stretchable strip is characterized by different surface roughnesses along its length.

It is another object of the present invention to provide the method as defined above, additionally comprising step of fitting each of said at least one laparoscopic instruments with at least one of said wireless transmitters.

It is another object of the present invention to provide the method as defined above, wherein said wireless transmitter is adapted to locate the position of at least one of said laparoscopic instruments.

It is another object of the present invention to provide the method as defined above, additionally comprising step of confirming a selection of said at least one laparoscopic instrument by clicking on said at least one wearable operator It is another object of the present invention to provide the method as defined above, additionally comprising step of activating said at least one wearable operator by depression on the same, voice activating the same, prolonged depression on the same, double clicking on the same and any combination thereof.

It is another object of the present invention to provide the method as defined above, additionally comprising step of directing an endoscope to said laparoscopic instrument by using image information shown on a video screen by means of said computerized platform configured without said help of assistants.

It is another object of the present invention to provide a wearable operator, comprising:
  a. at least two portions at least partially overlapping each other; said two portion are adapted to rotate and tilt relative to each other;
  b. at least one wireless transmitter, adapted to transmit a signal once said at least one wearable operator is activated.

It is another object of the present invention to provide the wearable operator as defined above, wherein said wearable operator is worn by a user on a predetermined body part, such that activation of said wearable operator results in activation of an external instrument.

It is another object of the present invention to provide the wearable operator as defined above, wherein said predetermined body part is selected from a group consisting of: the hand of said surgeon, at least one of the fingers of said user, the thigh of said user, the neck of said user, at least one of the legs of said user, the knee of said user, the head of said user and any combination thereof.

It is another object of the present invention to provide the wearable operator as defined above, wherein said wearable operator is coupled to a predetermined location on an instrument by means of an adaptor, such that activation of said wearable operator results in activation of said instrument.

It is another object of the present invention to provide the wearable operator as defined above, wherein said coupling between said at least one of said wearable operators and said instrument is either wire or wirelessly coupling.

It is still an object of the present invention to provide the wearable operator as defined above, wherein said wearable operator comprises (a) at least one flexible and stretchable strip; and, (b) loop-closing means adapted to close a loop with said at least one flexible and stretchable strip; said at least one flexible and stretchable strip and said loop-closing means are provided so as to fit said wearable operator to at least one selected from a group consisting of (a) said predetermined location of said different instruments; (b) said predetermined body part of said user, each of which is characterized by a different size and shape.

It is lastly an object of the present invention to provide the wearable operator as defined above, wherein the shape of said wearable operator is selected from a group consisting of a ring, a bracelet and any combination thereof.

BRIEF DESCRIPTION OF THE FIGURES

In order to understand the invention and to see how it may be implemented in practice, and by way of non-limiting example only, with reference to the accompanying drawing, in which

FIG. 7a-7b is an illustration of a wearable operator;

FIG. 8 is a general schematic view of an enhanced interface laparoscopic system that relies on at least two wireless signals to indicate the instrument on which to focus the endoscope;

FIG. 15a-15b illustrates the 'adjustability' of the wearable operator.

DETAILED DESCRIPTION OF THE EMBODIMENTS

Figure 1:
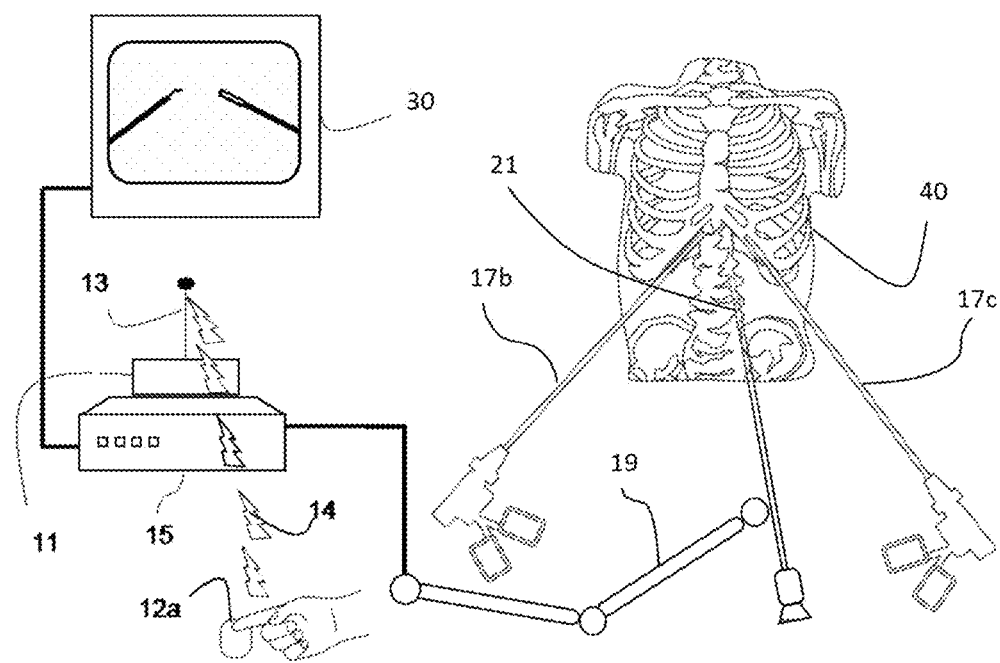
FIG. 1 is a general schematic view of an enhanced interface laparoscopic system that relies on a single wireless code signal to indicate the instrument on which to focus the endoscope constructed in accordance with the principles of the present invention in a preferred embodiment thereof.

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide means and methods for improving the interface between the surgeon and an endoscope system for laparoscopic surgery.

The present invention can be also utilized to improve the interface between the surgeon and the operating medical assistant and/or the surgeon colleagues. Moreover, the present invention can be also utilized to control and/or direct an automated endoscope assistant to focus the endoscope to the desired instrument of the surgeon. In some embodiments, it comprises a wearable user interface operator (referred to also as the 'wearable operator'). Furthermore, the device is adapted to focus the operating medical assistant on the desired instrument of the surgeon.

The term "conventional laparoscopy computerized system" refers herein to system or/software conventionally used in the market such as Lapman, Endo assist or AESOP.

The term "tight-fit" refers herein to a fit between two parts, such that said two parts are considered as coupled together.

The device of the present invention is adapted to control and/or direct the automated endoscope assistant to focus the endoscope on the instrument desired by the surgeon. In preferred embodiments, it comprises a wearable user interface to enable to operator to activate and select tools.

The present invention can be also utilized to improve the interface between the surgeon and the operating medical assistant and/or the surgeon's colleagues. Moreover, the present invention can be also utilized to control and/or direct an automated endoscope assistant to focus the endoscope on the desired instrument of the surgeon via output from the wearable operator, said output controlled by the surgeon. Furthermore, the device is adapted to direct the operating medical assistant to focus on the desired instrument of the surgeon.

In general, the present invention, an enhanced interface laparoscopy device comprises:
a. at least one operator comprising at least one wireless transmitter.
b. at least one wireless receiver.
c. at least one conventional laparoscopy computerized system; the conventional laparoscopy computerized system is adapted to load a surgical instrument's spatial locating software, and an automated assistant's maneuvering software; the locating software enables a visual response to a primary activation of the wireless transmitter; said maneuvering software enables the movement of said endoscope.
d. At least one video screen.
e. At least one automated assistant.

The device of the present invention has many technological advantages, among them:
Simplifying the communication interface between surgeon and mechanical assistants.
Seamless interaction with conventional computerized automated endoscope systems.
Simplicity of construction and reliability.
User-friendliness.

Additional features and advantages of the invention will become apparent from the following drawings and description.

In preferred embodiment of the invention a single wireless emission code is utilized and choice is achieved by a visible graphic representation upon the conventional viewing screen.

In another preferred embodiment each instrument is fitted with a unique code wireless transmitter, and selection is achieved by depressing its button.

According to another preferred embodiment, each instrument is fitted with a unique code wireless transmitter, and selection is achieved by depressing a control on the wearable operator.

The present invention discloses also a device joined with conventional camera assisted laparoscopic surgery systems comprising at least one wireless transmitter that can but need not be attached to the maneuvering control end of surgical instruments.

Selection of an instrument can be either via a control on a wireless transmitter, or via a wearable operator, or by a combination thereof. If control is via at least one button on at least one wireless transmitter, upon depression of a button on a transmitter either a generic or a unique code is transmitted to a receiving device connected to a computer that presents (e.g. displays) the selected surgical tool on a connected video screen. Confirmation of the selection by the depression of at least one button on the wireless transmitter transmits a code to the receiver connected to the computer that instructs the automated surgical assistant to move the endoscope achieving a view on the screen that is focused on the selected instrument area.

If control is via a wearable controller, upon activation (e.g., depression) of a control on the wearable operator, either a generic or a unique code is transmitted to a receiving device connected to a computer that presents (e.g. displays) the selected surgical tool on a connected video screen.

After confirmation of the selection by the depression of at least one button in the wearable operator's wireless transmitter, a code is transmitted to the receiver connected to the computer that instructs the automated surgical assistant to move the endoscope, achieving a view on the screen that is focused on the selected instrument area.

It would thus be desirable to achieve a device that allows the surgeon to identify to the laparoscopic computing system as well as to surgical colleagues to which surgical instrument attention is to be directed. By identifying the surgical instrument by the laparoscopic computing system the endoscope directs the view to the selected focus of attention.

Therefore, in accordance with one embodiment of the present invention an enhanced interface laparoscopy device is provided. The device comprises:
a. At least one wireless transmitter with at least one operating key.
b. At least one wireless receiver.
c. at least one conventional laparoscopy computerized system; said conventional laparoscopy computerized system is adapted to load a surgical instrument spatial locating software, and an automated assistant maneuvering software; said locating software enables a visual response to the depression of said at least one key on said wireless transmitter; said maneuvering software enables the movement of said endoscope.
d. At least one video screen.
e. At least one automated assistant.

In a further embodiment of the enhanced interface laparoscopy device the wireless transmitter or transmitters are either freestanding or attached to the maneuvering end of the surgical instruments and emit the same single code that upon the depression of at least one key on them emits a signal to the receiver that communicates with the connected computer that displays a graphic symbol upon a random choice of one of the onscreen surgical instruments depicted or extracted by the computer on the screen. If needed the surgeon repeats the depression of at least one key resulting in a shift in the displayed graphic designator from one onscreen depiction of surgical instrument to another until the desired instrument is reached and thereby selected. Subsequently the computer directs the automated assistant to focus the endoscope on the desired instrument area.

In a further embodiment the selection of the instrument requires confirmation by varying the form of click on at least one key, such as a prolonged depression. Only upon confirmation is the computer authorized to instruct the automated assistant to focus the endoscope on the desired instrument area.

In another embodiment of the invention each relevant surgical instrument is fitted at its maneuvering control end with a wireless transmitter with at least one key that transmits a unique code. In the initial stage of the procedure the surgeon identifies each of the instruments to the computerized system by depressing at least one key on each of the wireless transmitters fitted to the surgical instruments and matching their characteristics with a prepared database, thereby forming within the computerized system a unique signature for each of the transmitters. Thereon, upon depression of at least one key on the wireless transmitter attached to each surgical instrument, the receiver receives the unique code communicates it to the computer that identifies it with the preprogrammed signature and instructs the automated assistant to move the endoscope so as to achieve the desired focus.

In another embodiment of the invention each relevant surgical instruments is fitted at its maneuvering control end with a wireless transmitter with at least one key that transmits a unique code. While performing the surgery procedure, whenever the surgeon inserts, a surgical instrument at the first time, he signals by depressing at least one key on each of the wireless transmitters fitted to the surgical instruments. Then the computer software identifies the instrument, while it is being inserted, analyzes the characteristics of the surgical instrument and keeps it in a database, thereby forming within the computerized system a unique signature for each of the transmitters. Thereon, upon depression of at least one key on the wireless transmitter attached to each surgical instrument, the receiver receives the unique code, communicates it to the computer that identifies it with the signature stored at the insertion step and instructs the automated assistant to move the endoscope so as to achieve the desired focus.

In a further embodiment the selection is signified on the connected screen by displaying a graphic symbol upon the onscreen depiction of the surgical instrument.

In a further embodiment the selection is confirmed by an additional mode of depression of at least one key on the wireless transmitter, such as a prolonged depression of the key, authorizing the computer to instruct the automated assistant to change view provided by the endoscope. The device of the present invention has many technological advantages, among them:
  Simplifying the communication interface between surgeon and mechanical assistants.
  Seamless interaction with conventional computerized automated endoscope systems.
  Simplicity of construction and reliability.
  User-friendliness
  Additional features and advantages of the invention will become apparent from the following drawings and description.

Reference is made now to FIG. 1, which is a general schematic view of an enhanced interface laparoscopic system comprising one or more button operated wireless transmitters 12a, that may or may not be attached to the maneuvering end of surgical instruments 17b and 17c, which once depressed aerially transmit a single code wave 14 through aerial 13 to connected receiver 11 that produces a signal processed by computer 15 thereby assigning a particular one of two or more surgical instruments 17b and 17c as the focus of the surgeons attention. Accordingly a conventional automated endoscope 21 is maneuvered by means of conventional automated arm 19 according to conventional computational spatial placement software contained in computer 15.

Figure 2:
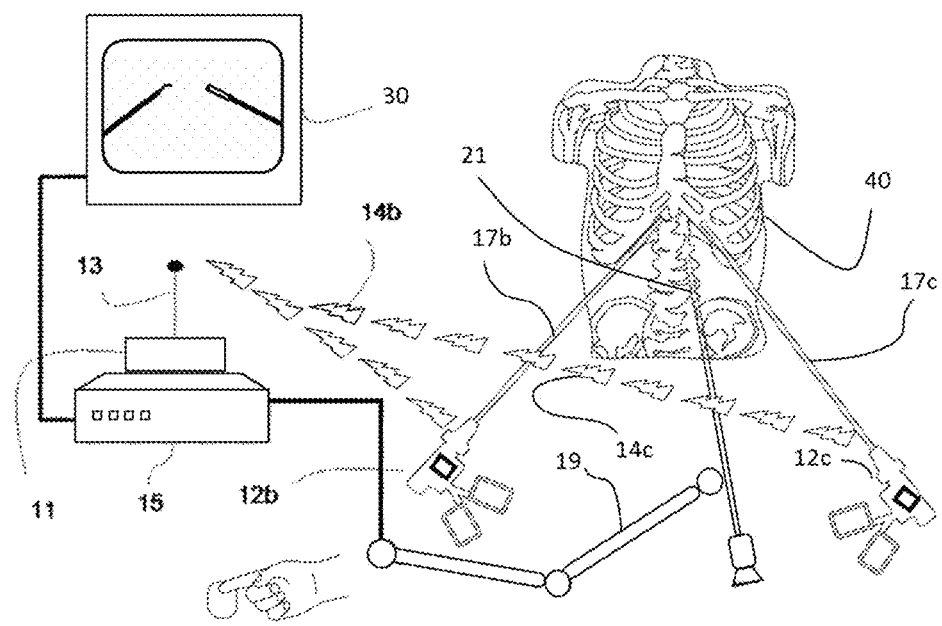
FIG. 2 is a general schematic view of an enhanced interface laparoscopic system that relies on at least two wireless signals to indicate the instrument on which to focus the endoscope.

Reference is made now to FIG. 2, which is a general schematic view of an enhanced interface laparoscopic system comprising one or more button operated wireless transmitters 12b and 12c are attached respectfully to the maneuvering means at the end of surgical instruments 17b and 17c, which once depressed aerially, each transmit a unique code wave 14b and 14c through aerial 13 to connected receiver 11 that produces a signal processed by computer 15 thereby assigning a particular one of two or more surgical instruments 17b and 17c as the focus of the surgeons attention. Accordingly a conventional automated endoscope 21 is maneuvered by means of conventional automated arm 19 according to conventional computational spatial placement software contained in computer 15.

Figure 3:
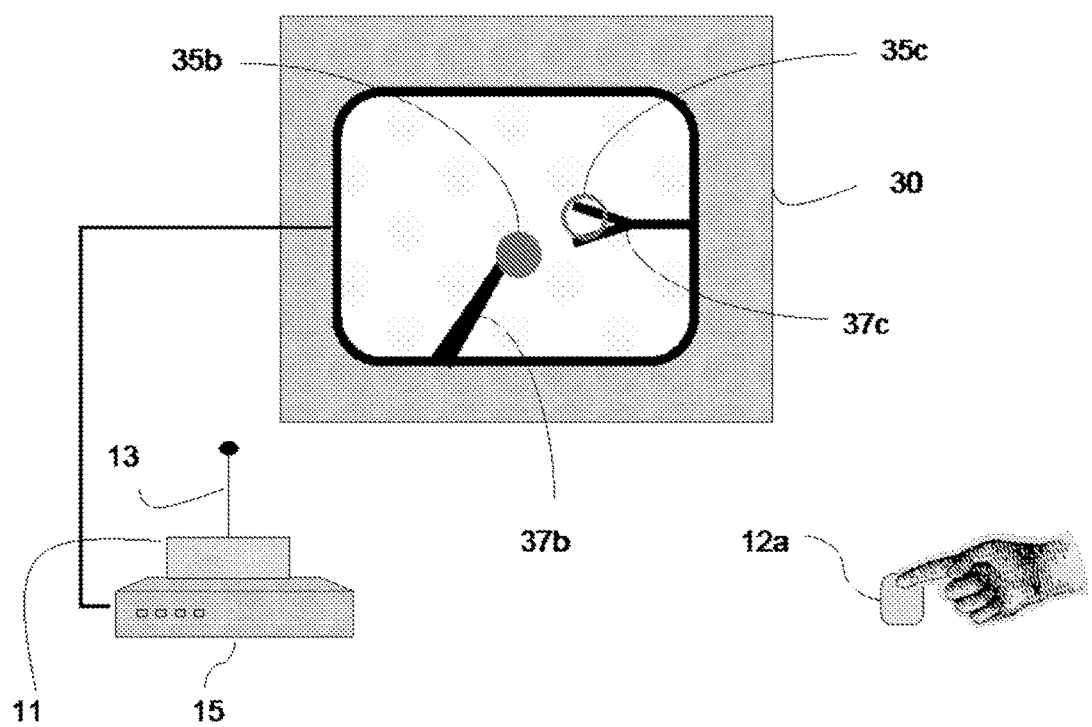
FIG. 3 is a schematic view of the method in which the single wireless code signal choice instrumentation focus is represented on the viewing apparatus.

Reference is made now to FIG. 3, which is a schematic view of the method in which single wireless signal code choice of instrumentation focus is achieved, by means of video representation, 35b and 35c of the actual surgical instruments (not represented in FIG. 3) displayed by graphic symbols. Wherein a light depression of the button on generic code emitting wireless transmitter 12a transmits a code that is received by receiver aerial 13 communicated through connected receiver 11 to computer 15 that shifts the graphically displayed symbol of choice 35b on video screen 30 from instrument to instrument until the required instrument is reached. A prolonged depression of the button on transmitter 12a confirms the selection thereby signaling computer 15 to instruct the automated mechanical assistant (not represented in FIG. 4) to move the endoscope (not represented in FIG. 3) and achieving a camera view of the instrument area on screen 30.

Figure 4:
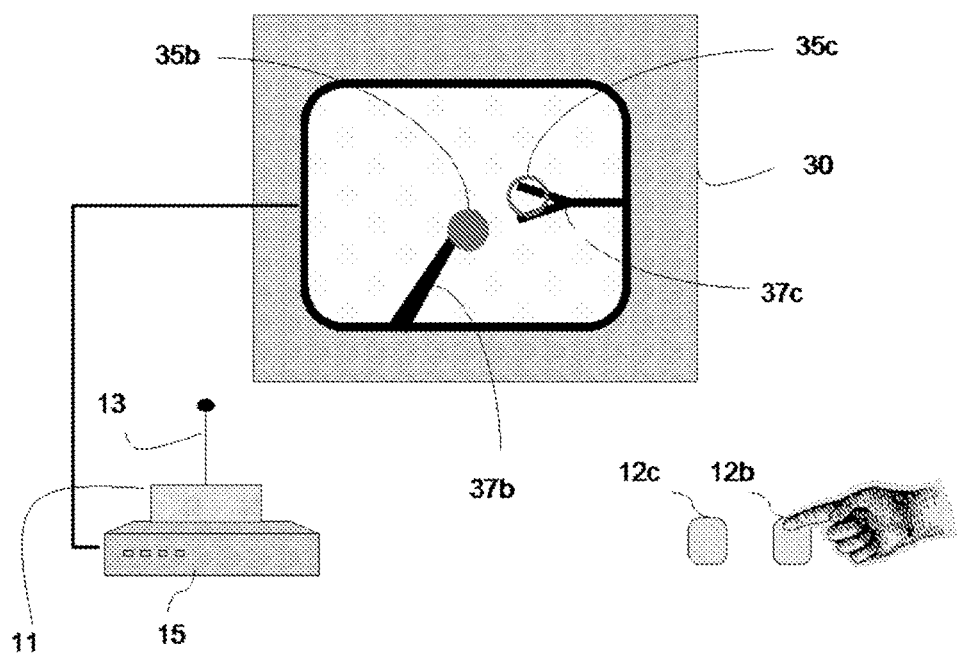
FIG. 4 is a schematic view of the method in which multiple wireless code signal choice of instrumentation is operated.

Reference is made now to FIG. 4, which is a schematic view of the method in which multiple wireless signal code choice of instrumentation focus is achieved, by means of video representation 35b and 35c of the actual surgical instruments (not represented in FIG. 4) displayed by graphic symbols. Wherein when buttons on unique code emitting wireless transmitters 12b and 12c attached respectively to actual operational instruments (not represented in FIG. 4) displays graphic symbol 35b on respective video representation 37b. A prolonged depression of the button on transmitter 12b and 12c confirms the selection thereby signaling computer 15 to instruct the automated mechanical assistant (not represented in FIG. 4) to move the endoscope (not represented in FIG. 4) and achieving a camera view of the instrument area on screen 30.

In another embodiment of this invention, when a prolonged depression of the buttons on transmitter 12b and 12c confirms the selection, the computer software analyze the characteristics of the surgical instrument and stores it in a database, thereby forming within the computerized system, a database, used for matching between each transmitting code and a surgical instrument.

From now on, when the surgeon presses again on this button, the receiver that receives the transmitted code, communicates it to the computer software that identifies the code as a "known" code and matching it, to the known parameters that were stored earlier in database of the surgical tools, and extracts the surgical tool tip. When the position tool tip is known, then the tracking software instructs the automated assistant to move the endoscope so as to achieve the desired focus.

Figure 5:
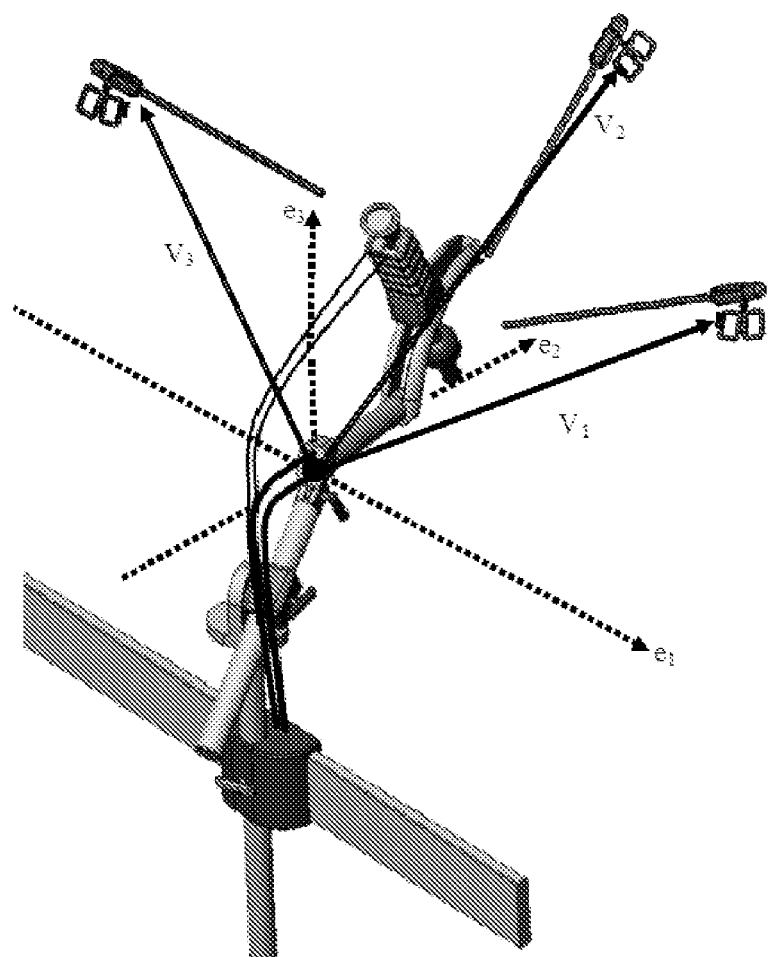
FIG. 5 represents the relative position of each tool in respect to the mechanism.

Reference is made now to FIG. 5 illustrating the relative position of each tool. While performing the surgery, the surgeon often changes the position of his tools and even their insertion point. The wireless transmitters then may be use to locate the relative angle in which each tool is being held in respect to the camera holder mechanism. This is another advantage of the system that is used to calculate the position of the tool in the frame captured by the video camera. In that manner the surgeon does not have to inform the system where the insertion point of every tool is. The exact location of the wireless transmitter is not measured: the information about the relative positions of the tools in respect to each other contains in most cases enough data for the software to maintain the matching between the transmitters and the tools. In this figure the positioning sensors of the system are placed near or on the camera holder so the signals they receive can be utilize in order to calculate the vectors V1 V2 . . . Vn representing the range and the 3 angles needed to define a point in a 3D space.

In order to realize a position and range system, many well known technologies may be used. For example if the transmitters emit wireless signals then an array of antennas may be used to compare the power of the signal received at each antenna in order to determine the angle of the transmitter and it's approximate range to the camera holder mechanism. If the transmitter emits ultra sound wave then US microphones can be used to triangulate the position of the transmitter. The same is for light emitting transmitter.

Therefore, in accordance with a preferred embodiment of the present invention, an enhanced interface laparoscopy device is provided. The device comprises:

a. at least one endoscope, mechanically interconnected to said automated assistant; said automated assistant is adapted to maneuver said endoscope to a desired location;
b. at least one instrument;
c. at least one wearable operator comprising at least one wireless transmitter, adapted to transmit a signal once said at least one wearable operator is activated; said at least one wearable operator is either wire or wirelessly in communication with said at least one of said instrument;
d. at least one wireless receiver adapted to receive said signal sent by said transmitter;
e. at least one laparoscopy computerized system, in communication with said wireless receiver, adapted to provide a visual onscreen depiction of said at least one instrument to be selected following the activation of said at least one wearable operator; and,
f. at least one video screen wherein said device is adapted to control and to direct said endoscope via said laparoscopy computerized system and said automated assistant on said instrument, said instrument to be selected following the activation of said at least one wearable operator.

According to one embodiment, the wearable user interface is attached to the operating tool.

According to another embodiment, the interface is linked/attached to a predetermined body part of the surgeon. Said body part is selected from a group consisting of: the hand of the surgeon, at least one of the fingers of the surgeon, the thigh of the surgeon, the neck of the surgeon, at least one of the legs of the surgeon, the knee of the surgeon, the head of the surgeon and any combination thereof.

In a preferred embodiment of the enhanced interface laparoscopy device, the wireless transmitter or transmitters are either freestanding or are attached to the maneuvering end of the surgical instruments. They emit the same single code so that, upon the activation (e.g., depression) of the wearable operator, they emit a signal to the receiver. The receiver communicates with a connected computer that displays a graphic symbol upon one of one of the surgical instruments depicted on the screen by the computer. On initial activation, the graphical symbol can be displayed on a randomly-chosen surgical instrument, or it can be displayed on a predefined surgical instrument.

If needed, the surgeon repeats the activation (e.g., depression) of the wearable operator resulting in a shift in the displayed graphic designator from one onscreen depiction of a surgical instrument to another until the desired instrument is reached and thereby selected. Subsequently the computer directs the automated assistant to focus the endoscope on the desired instrument area.

In a further preferred embodiment the selection of the instrument requires confirmation by varying the form of activating said wearable operator, such as a prolonged depression, double clicking or voice activation. Only upon confirmation is the computer authorized to instruct the automated assistant to focus the endoscope on the desired instrument area.

In another preferred embodiment of the invention each relevant surgical instrument is fitted at its maneuvering control end with a wireless transmitter that transmits a unique code.

In the initial stage of the procedure, the surgeon identifies each of the instruments to the computerized system by activating the wearable operator (e.g., depressing at least one key on the same) on each of the wireless transmitters fitted to the surgical instruments and matching their characteristics with a prepared database, thereby forming within the computerized system a unique signature for each of the transmitters.

Thereon, upon depression of the wearable operator attached to each surgical instrument/or on the surgeon's hand, the receiver receives the unique code, and communicates it to the computer. The computer identifies it with the preprogrammed signature and instructs the automated assistant to move the endoscope so as to achieve the desired focus.

It should be pointed out that the wearable operator can be coupled to a predetermined body part selected from a group consisting of: the hand of said surgeon, at least one of the fingers of the surgeon, the thigh of the surgeon, the neck of the surgeon, at least one of the legs of the surgeon, the knee of the surgeon, the head of the surgeon and any combination thereof.

In another preferred embodiment of the invention, each relevant surgical instrument is fitted at its maneuvering control end with a wireless transmitter (as part of the wearable operator) that transmits a unique code. While performing the surgical procedure, whenever the surgeon inserts a surgical instrument for the first time, he signals by activating the wearable operator so as to uniquely identify the surgical instrument.

According to one embodiment of the present invention, the wearable operator comprises an activating button, such that the activation of the same can be achieved by manually pressing the same.

According to another embodiment of the present invention, the wearable operator is activated manually or automatically.

According to one embodiment of the present invention, the activation of the wearable operator is achieved by means of depression on the same, voice activating the same, prolonged depression on the same, double clicking on the same and any combination thereof.

When the instrument is being inserted for the first time, the computer software identifies the instrument, analyzes the characteristics of the surgical instrument and keeps the characteristics in a database, thereby forming within the computerized system a unique signature for each of the instruments. Thereafter, upon activation of the wireless transmitter attached to each surgical instrument, the receiver receives the unique code, communicates it to the computer that identifies it with the signature stored at the insertion step and instructs the automated assistant to move the endoscope so as to achieve the desired focus.

In a further preferred embodiment, the selection is signified on the screen connected to the computer by displaying a graphic symbol upon the onscreen depiction of the surgical instrument.

In a further preferred embodiment the selection is confirmed by an additional mode of depression on the wireless transmitter, such as a prolonged depression of the wearable operator, authorizing the computer to instruct the automated assistant to change the view provided by the endoscope.

The device of the present invention has many technological advantages, among them:

Simplifying the communication interface between surgeon and mechanical assistants.

Seamless interaction with conventional computerized automated endoscope systems.

Simplicity of construction and reliability.

User-friendliness

Figure 6:
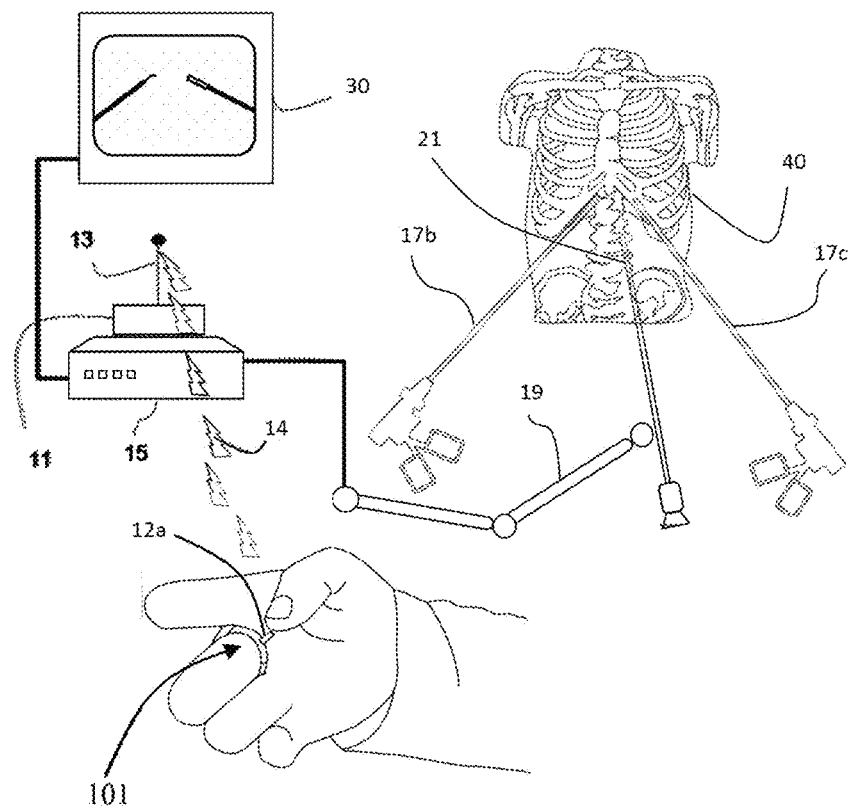
FIG. 6 is a general schematic view of an enhanced interface laparoscopic system that relies on a single wireless code signal to indicate the instrument on which to focus the endoscope, constructed in accordance with the principles of the present invention in a preferred embodiment thereof.

Reference is made now to FIG. 6, which is a general schematic view of an enhanced interface laparoscopic system comprising one or more wearable operators 101 (each of which comprises wireless transmitters 12a), that is worn by the surgeon (e.g., integrated within a bracelet or a ring).

Once the same is activated (e.g., depressed), it wirelessly transmits a single code wave 14 through aerial 13 to connected receiver 11 that produces a signal processed by computer 15, thereby assigning a particular code to one of two or more surgical instruments 17b and 17c within the patient 40 as the focus of the surgeon's attention.

Reference is now made to FIGS. 7a-7b which illustrate a preferred embodiment of the wearable operator of the present invention.

According to this embodiment, the wearable operator is configured as a ring (FIG. 7a) to be worn on the surgeon's finger (see FIG. 7b).

According to this embodiment, the wearable operator comprises a pressing key 100 (also referred to as pressing button 101d). Once the surgeon wishes to re-orient the endoscope so as to focus on the desired instrument (linked to said wearable operator), the surgeon presses the same.

FIG. 7a illustrates the wearable operator 101, in its ring-like configuration.

FIG. 7b illustrates the wearable operator 101, as worn by the surgeon.

According to another embodiment or the present invention, the wearable actuator may be attached to the maneuvering end of surgical instruments 17b and 17c.

It is appreciated that each surgical instrument has particular dimensions. Therefore, since there isn't a 'universal' shape of surgical instruments, each surgical instrument should be provided with a dedicated wearable operator. Thus, according to one embodiment of the present invention, a dedicated wearable operator is provided for each instrument.

According to another embodiment of the present invention, a universal adaptor to be attached to any surgical instrument is provided (see further detail with respect to FIGS. 11a-11e hereinbelow).

Once the wearable operator is operated, a conventional automated endoscope 21 is maneuvered by means of conventional automated arm 19 according to conventional computational spatial placement software contained in computer 15

Reference is made now to FIG. 8, which is a general schematic view of an enhanced interface laparoscopic system comprising one or more wearable operators (not shown in the figure). According to this embodiment, the wearable operators are worn on the surgical instrument. As described above, each of said wearable operators comprises a wireless transmitter (12b and 12c).

Each of the wireless transmitters 12b and 12c is attached, respectively, to the maneuvering means at the end of surgical instruments 17b and 17c, within the patient 40. Once the wearable operator is activated (e.g., depressed), each transmits a unique code wave 14b and 14c through aerial 13 to connected receiver 11 that produces a signal processed by computer 15, thereby assigning a particular one of two or more surgical instruments 17b and 17c as the focus of the surgeon's attention. Accordingly, a conventional automated endoscope 21 is maneuvered by means of conventional automated arm 19 according to conventional computational spatial placement software contained in computer 15.

Figure 9:
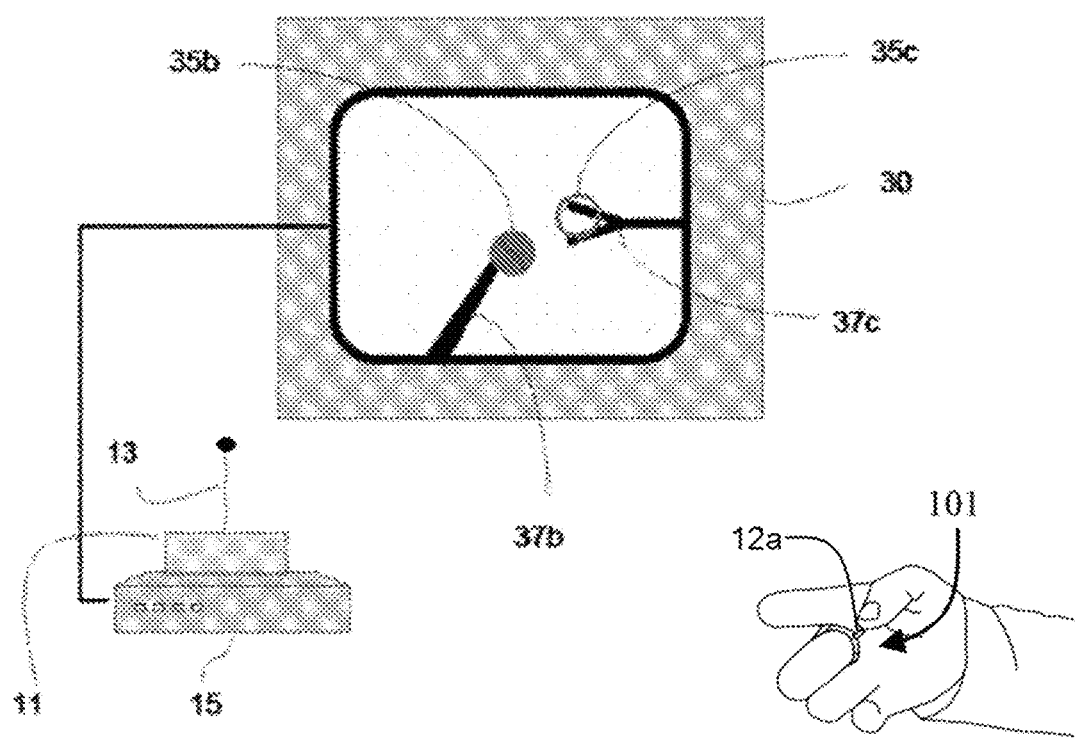
FIG. 9 is a schematic view of the method in which choice of instrumentation focus via a single wireless code is represented on the viewing apparatus.

Reference is made now to FIG. 9, which is a schematic view of a method by which choice of instrumentation focus is achieved with a single wireless signal code, by means of a display on a video screen of video representations 37b and 37c of the actual surgical instruments, and graphical symbols 35b and 35c. In this non-limiting example, solid circle 35b indicates a selected instrument, while open circle 35c indicates an activated but non-selected instrument.

In this embodiment, on activation of the wearable operator 101 (e.g., by a light depression of the button on the wearable operator), wireless transmitter 12a emits a generic code that is received by receiver aerial 13 and communicated through connected receiver 11 to computer 15. Computer 15 shifts the graphically displayed symbol of choice 35b on video screen 30 from instrument to instrument until the required instrument is reached.

In this example, the wearable operator 101 is shaped as a ring and is worn on the surgeon's finger.

A prolonged depression of the wearable operator 101 confirms the selection, thereby signaling computer 15 to instruct the automated mechanical assistant to move the endoscope and achieve a camera view of the instrument area on screen 30.

Figure 10:
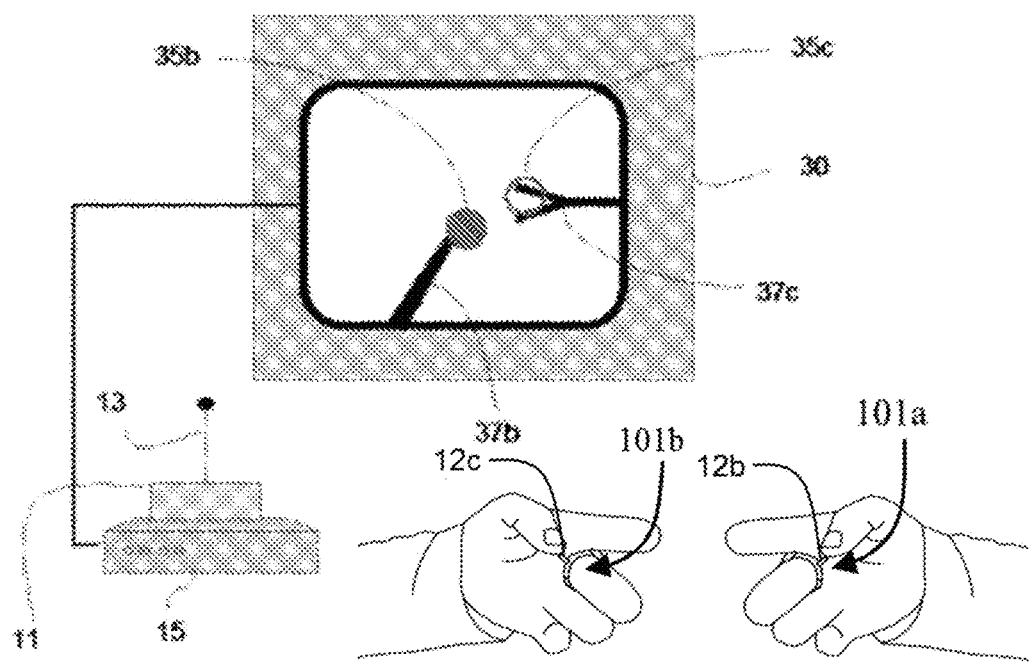
FIG. 10 is a schematic view of the method in which choice of instrumentation focus via a multiple wireless code is operated.

Reference is made now to FIG. 10, which is a schematic view of a method in which choice of instrumentation focus is achieved in the case where there are multiple wireless signal codes, by means of a display on a video screen of video representations 37b and 37c of the actual surgical instruments, and graphical symbols 35b and 35c.

When the wearable operators 101a and 101b (and the wireless transmitters 12b and 12c, respectively) are being pressed, the same emit a signal which eventually results in the display on screen 30 of graphic symbol 35b on respective video representation 37b or, alternatively, of graphic symbol 35c on video representation 37c.

Confirmation of the selection may be achieved by prolonged depression of a button located on the wearable operator. Thus, a prolonged depression of the button on the wearable operator confirms the selection, thereby signaling computer 15 to instruct the automated mechanical assistant (not represented in FIG. 4) to move the endoscope (not represented in FIG. 4) and achieve a camera view of the instrument area on screen 30.

In another embodiment of this invention, when a prolonged depression of the buttons on the wearable operator confirms the selection, the computer software analyzes the characteristics of the surgical instrument and stores it in a database, thereby forming, within the computerized system, a database used for matching between each transmitting code and its associated surgical instrument.

From now on, when the surgeon presses again on this button, the receiver that receives the transmitted code communicates it to the computer software that identifies the code as a "known" code, matches it to the known parameters that were stored earlier in the database of surgical tools, and extracts the position of the tip of the surgical tool. When the position of the tool tip is known, the tracking software instructs the automated assistant to move the endoscope so as to achieve the desired focus.

In another embodiment of this invention, when the wearable operator is activated and an instrument is selected, the computer software analyzes the characteristics of the surgical instrument and stores it in a database, thereby forming, within the computerized system, a database used for matching between each transmitting code and a surgical instrument.

From now on, when the surgeon activates the wearable activator, the receiver that receives the transmitted code communicates it to the computer software that identifies the code as a "known" code and matches it to the known parameters that were stored earlier in database of the surgical tools, and extracts the position of the tip of the surgical tool. When the position of the tool tip is known, the tracking software instructs the automated assistant to move the endoscope so as to achieve the desired focus.

Reference is now made to FIGS. 11a-11e illustrating another embodiment of the present invention.

As mentioned above, the wearable actuator may be attached to the maneuvering end of surgical instruments 17b and 17c. However, since each surgical instrument has particular dimensions, there is no 'universal' actuator that will fit every instrument. Thus, one should provide each of surgical instruments with a dedicated operator.

The present invention provides a universal adaptor 100 to be attached to the surgical instrument so as to overcome this disadvantage. The surgeon is able to couple the wearable operator 101 to the adaptor.

Figure 11A:
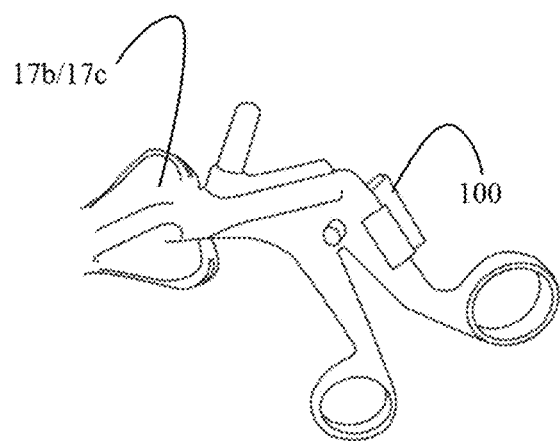
FIG. 11a-11e illustrates another preferred embodiment of the present invention.

Reference is now made to FIG. 11a which illustrates the surgical instrument 17b or 17c to which the adaptor 100 is being attached.

Figure 11B:
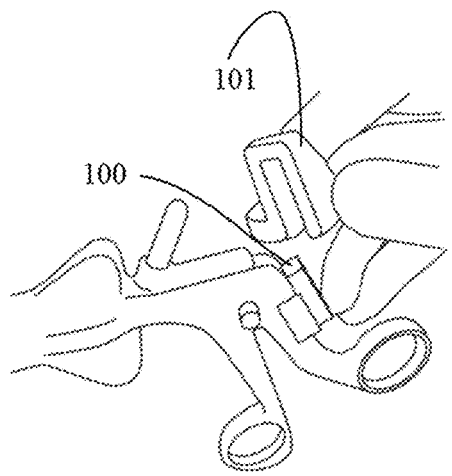

Reference is now made to FIG. 11b which illustrates the coupling of the wearable operator 101 to the universal adaptor 100.

Figure 11C:
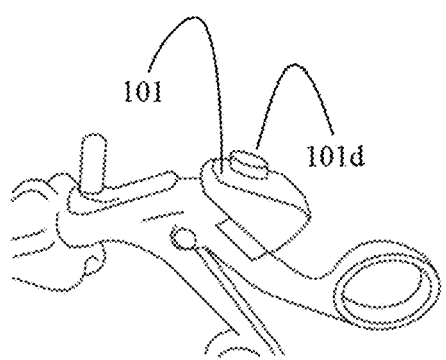

Reference is now made to FIG. 11c which illustrates the wearable operator 101 coupled to the adaptor and thus to the surgical instrument.

Figure 11D:
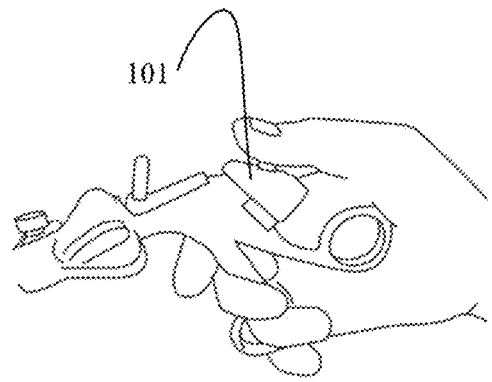

As mentioned above, according to one embodiment of the present invention, the wearable operator 101 comprises an activating button 101d (see FIG. 11c). Reference is now made to FIG. 11d which illustrates the activation of wearable operator 101. In FIG. 11d, activation is achieved by pressing on button 101d in wearable operator 101.

Figure 11E:
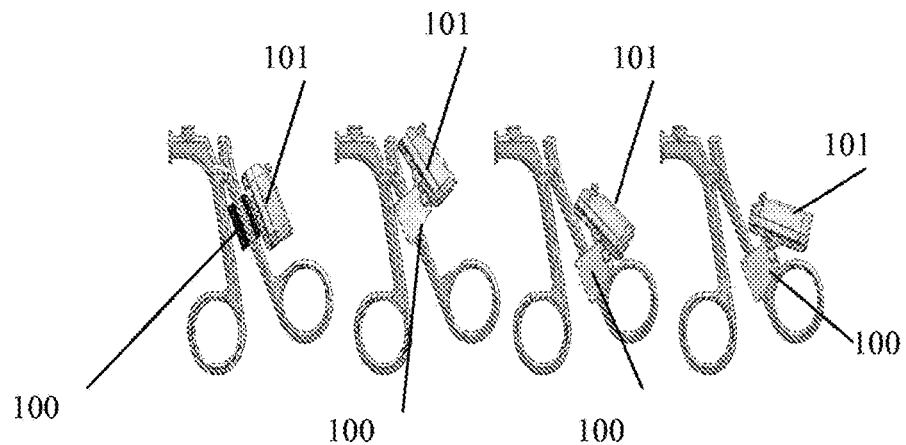

FIG. 11e illustrates different positions for the wearable operator 101 (and the adaptor 100) on the surgical instrument.

In order to realize a position and range system, many well-known technologies may be used. For example, if the transmitters emit wireless signals then an array of antennas may be used to compare the power of the signal received at each antenna in order to determine the angle of the transmitter and the approximate range (distance and angle) between it and the camera holder mechanism. If the transmitter emits ultrasound (US), then US microphones can be used to triangulate the position of the transmitter. The same can be done for light emitting transmitters.

Figure 12:
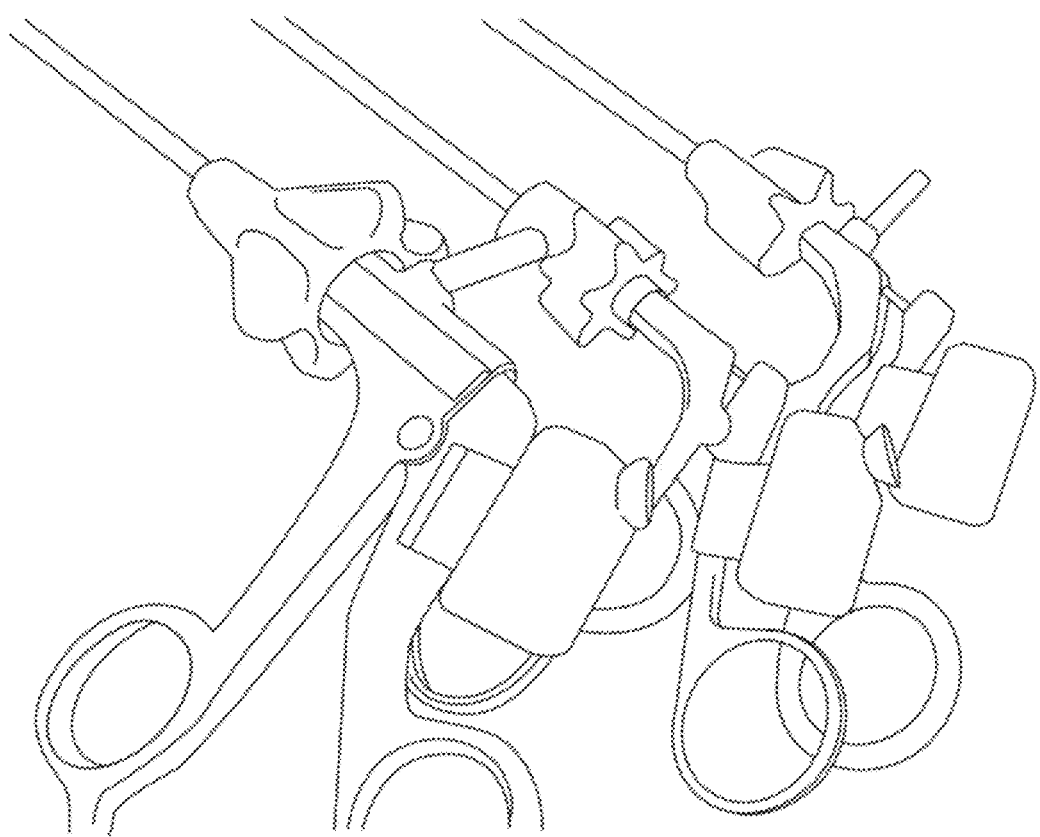
FIG. 12 illustrates the adjustability of the wearable operator.

Reference is now made to FIG. 12 which illustrates the adjustability of the wearable operator 101. As can be seen from the figure, the wearable operator 101 can be fitted to a variety of different tools, each of which is characterized by a different size and shape.

Reference is now made to FIGS. 13a-13e illustrating embodiments of the wearable operator 1300 and the adjustable means by which it may be attached to a surgical tool.

According to these embodiments, the wearable operator 1300 comprises a unidirectional coupling (e.g., ratchet 1310).

Once the wearable operator 1300 is secured to the surgical tool, the wearable operator 1300 is adjusted to the size and dimensions of the surgical tool by means of a unidirectional catch (e.g., ratchet 1310).

Figure 13A:
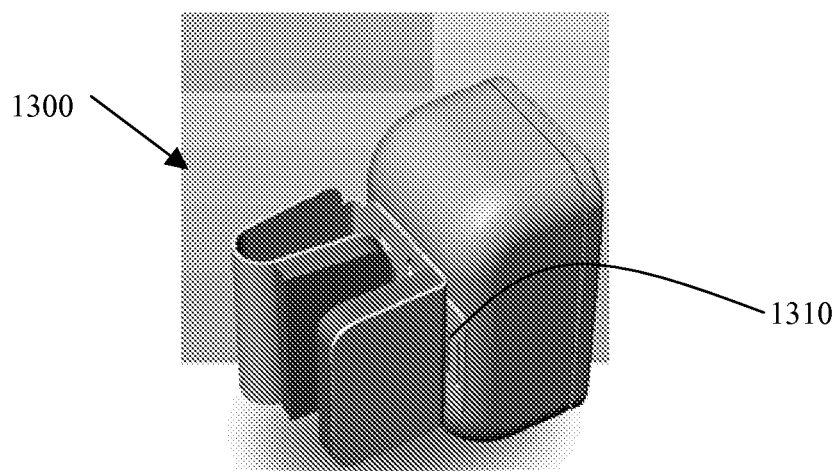
FIG. 13a-13e illustrates one embodiment of the wearable operator 700 and the adjustment means of the same to a surgical tool.
Figure 13B:
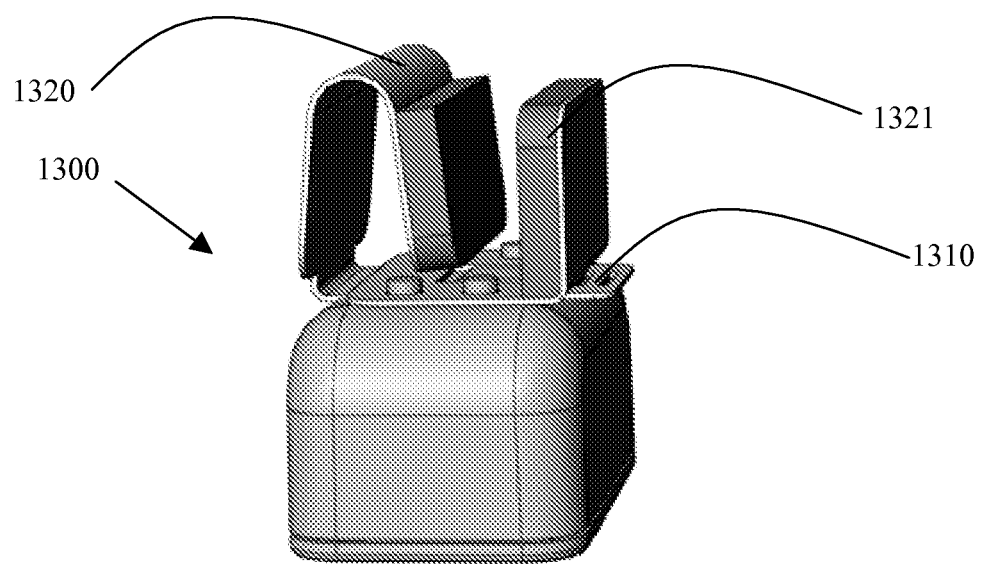
Figure 13C:
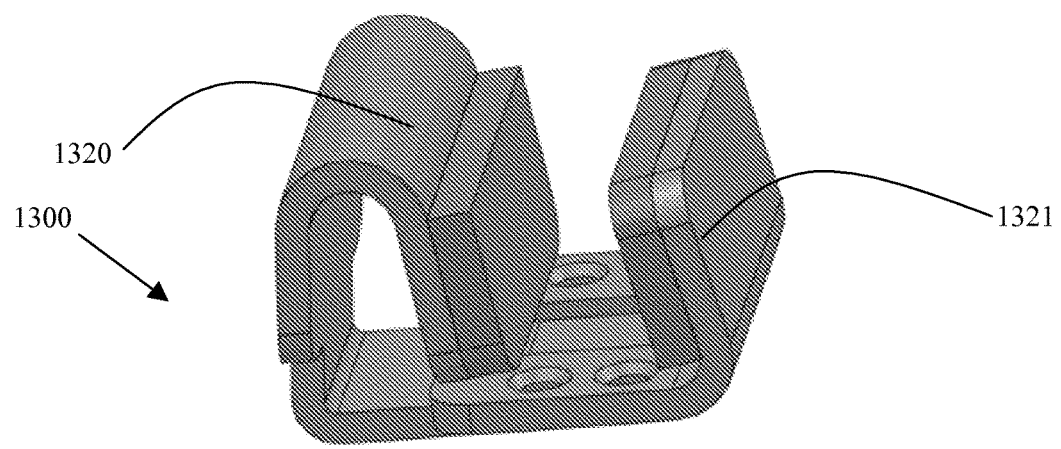

According to another embodiment, the wearable operator 1300 comprises a body having at least two portions 1320 and 1321 (see FIG. 13b). Said portions are adapted to 'grasp' the surgical tool such that when the wearable operator 1300 is coupled to the surgical tool, fine-tuned movement of the two body portions is obtainable so as to provide said tight-fit coupling between said two portions and said instrument.

According to another embodiment (FIG. 13c), one of the two portions (either 1320 or 1321) is rotationally movable relative to the other, such that when said wearable operator is coupled to said instrument, fine-tuned movement of said two body portions is obtainable so as to provide said tight-fit coupling between said two portions and said instrument.

According to another embodiment (FIG. 13d), the two portions (1321 and 1320) are rotationally movable relative to each other, such that when the wearable operator is coupled to said instrument, fine-tuned movement of said two body portions is obtainable so as to provide said tight-fit coupling between said two portions and said instrument.

Figure 13D:
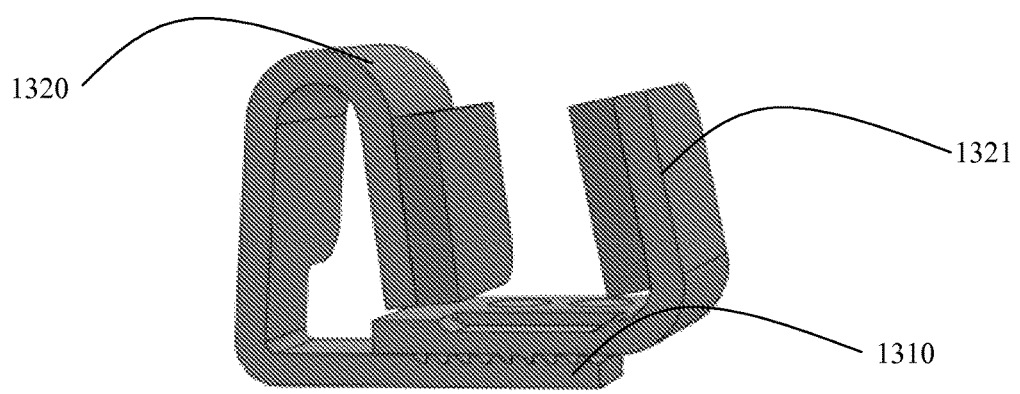

In reference to FIG. 13d, the movement of either portion 1320 or portion 1321 relative to the other is obtained by fixating the position of either portion 1320 or portion 1321 and coupling the other portion to e.g., a unidirectional catch (e.g., ratchet) 1310 or a two-way directional catch 1310 on the body of the wearable operator.

Figure 13E:
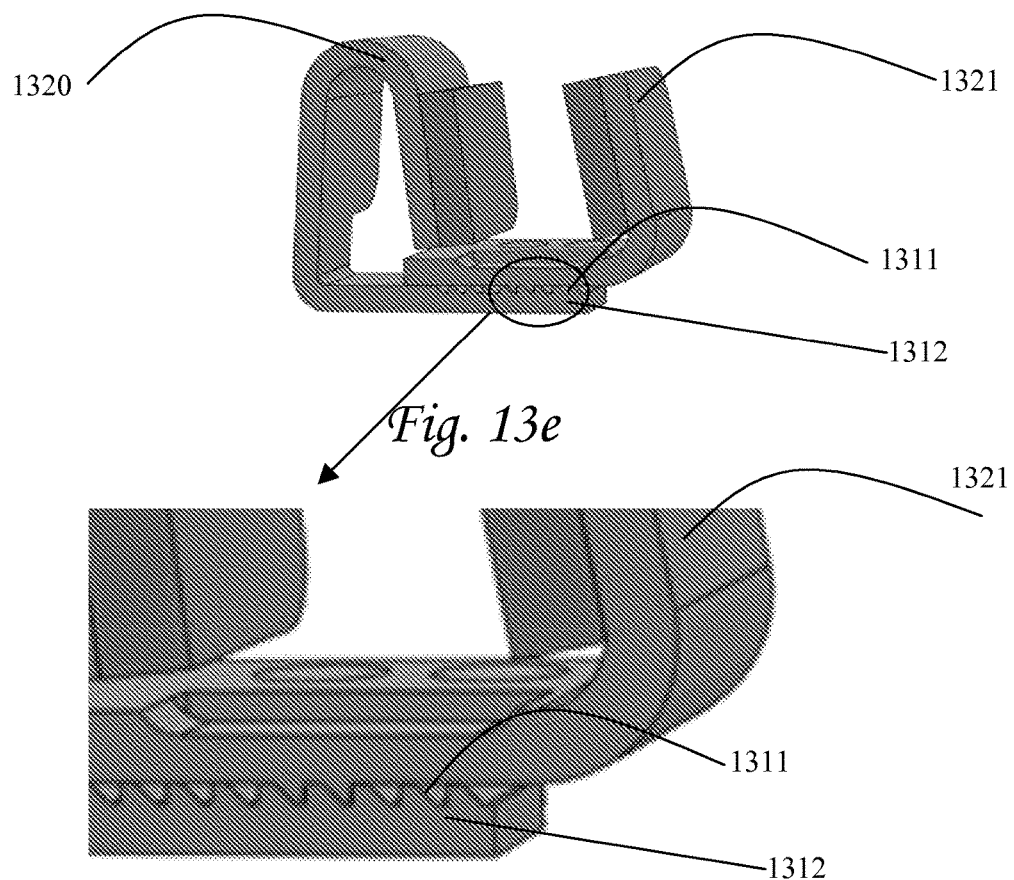

According to another embodiment, the movement of either portion 1320 or portion 1321 relative to the other is obtained by providing one portion, e.g., portion 1321 with cog-like teeth 1311 and the body of the wearable operator with cog-like teeth 1312 matching with cog-like teeth 1311 (see FIG. 13e). In such a way portion 1321 can be linearly moved relative to portion 1320.

According to another embodiment of the present invention, the wearable operator is a ring to be worn on the physician's hand.

Figure 14A:
FIG. 14a-14c, illustrates another embodiment of the present invention, which provides a best adjustment of the wearable operator to the operator's hand.
Figure 14B:
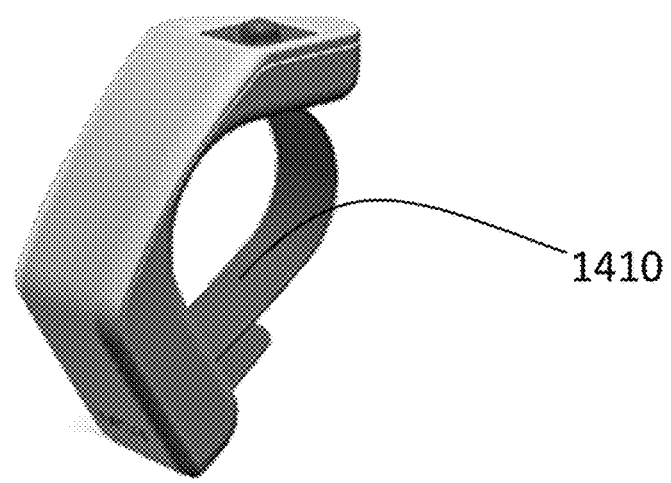
Figure 14C:
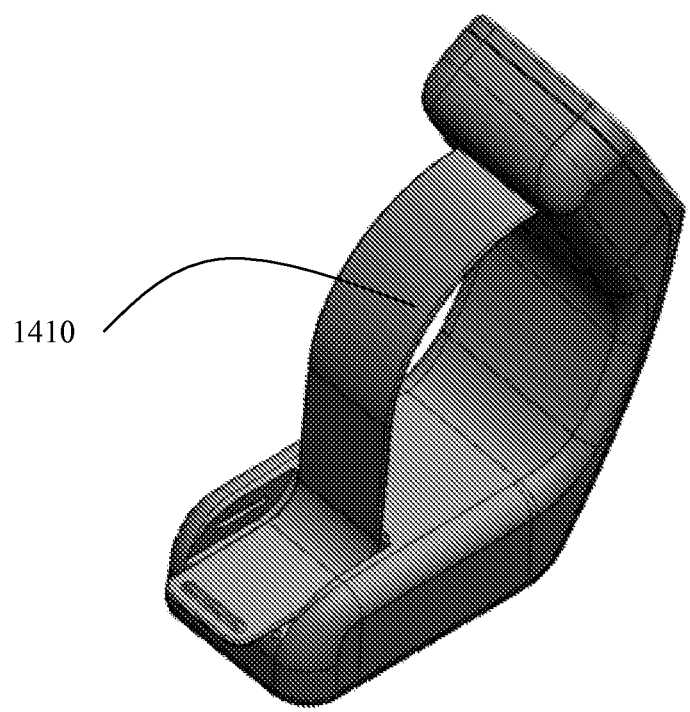

Reference is now made to FIGS. 14a-14c, illustrating another embodiment of the present invention, which provides the best adjustment of the wearable operator 1400 to the operator's hand. FIG. 14a illustrates the embodiment from the front, FIG. 14b illustrates it from the back, and FIG. 14c illustrates it from underneath. For illustrative purposes, the catch mechanism is not shown in FIG. 14c, According to another embodiment, the wearable operator 1400 is adjustable by means of flexible and stretchable silicone and/or rubber strip 1410 and a loop-closing means. The loop-closing means is adapted to close a loop with the flexible and stretchable strip. Together, the flexible and stretchable strip and the loop-closing means are provided so as to fit the wearable operator to at least one selected from a group consisting of (a) said predetermined location of said different instruments; (b) said predetermined body part of said surgeon, each of which is characterized by a different size and shape.

As will be disclosed hereinafter, the loop-closing means 1420 can be e.g., a unidirectional catch, a rack, a peg or any other mechanism known in the art.

According to another embodiment, the silicone and/or rubber strip 1410 is passed through a unidirectional catch (e.g., ratchet 1420), such that, when the physician wears the wearable operator 1400, he adjusts the same by pulling the silicone and/or rubber strip 1410 through the ratchet 1420.

According to another embodiment, the silicone and/or rubber strip 1410 is rotated around rack or peg 1420 such that, when the physician wears the wearable operator 1400, he adjusts the same by pulling the silicone and/or rubber strip 1410 around the peg 1420.

According to this embodiment, the silicone and/or rubber strip 1410 is characterized by a varied width along its length. More specifically, at least a portion of the silicone and/or rubber strip 1410 is characterized by a greater width, such that when the same is twisted/rotated around peg 1420 and reaches the wider portion, the same is fixedly secured to the wearable operator 1400.

According to another embodiment, the silicone and/or rubber strip 1410 is characterized by different surface roughnesses along its length. More specifically, at least a portion of the silicone and/or rubber strip 1410 is characterized by e.g., an abrasive or rough surface such that when the same is twisted/rotated around peg 1420 and reaches the rougher portion, the same is fixedly secured to the wearable operator 1400.

Figure 15A:
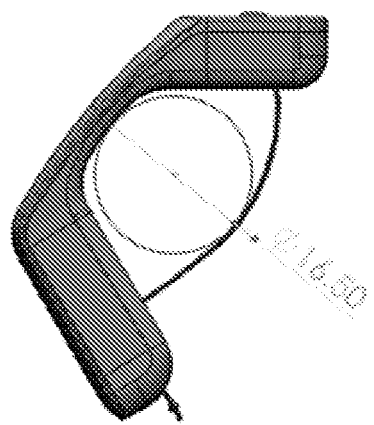
Figure 156:
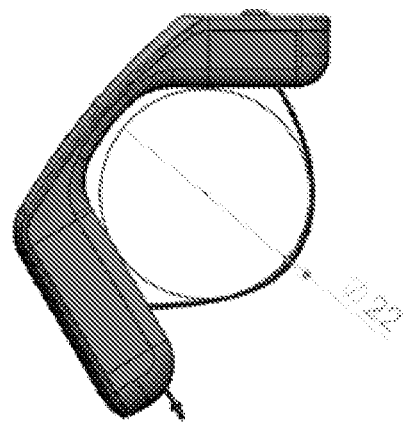

Reference is now made to FIGS. 15a-15b illustrating the 'adjustability' of the wearable operator. As can be seen, the wearable operator can be fit to and be secured to both 'wider' fingers (see FIG. 15b) and 'narrower' fingers (see FIG. 15a).

It is appreciated that certain features of the invention which are, for clarity, described in the context of separate embodiments, can also be provided in combination in a single embodiment. Conversely, various features of the invention which are, for brevity, described in the context of a single embodiment, can also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method for using an improved device for laparoscopic surgery, the method comprising:
   providing an improved device for laparoscopic surgery comprising:
      an endoscope mechanically connected to an automated assistant in a form of an automated arm, the automated assistant configured to move the endoscope into a desired position;
      at least one wearable operator having a wearable wireless transmitter including at least one operating key, the wearable wireless transmitter transmitting a first signal when the at least one operating key is activated by user action;
      one or more surgical instruments, each of the surgical instruments in communication with at least one wireless transmitter, wherein when the at least one operating key is activated the surgical instrument that the operating key is in communication with is selected as a surgical instrument that attention of a user of the device is focused on;
      a computer configured for laparoscopy in communication with the automated assistant in the form of an automated arm;
      at least one wireless receiver that receives the first signal, wherein upon receipt of the first signal produces a second signal and transmits the second signal to the computer; and
      a viewing screen in communication with the computer; wherein when the computer receives the second signal the computer performs at least one of the following:
         (i) selects the surgical instrument that attention of a user of the device is focused on;
         (ii) displays the selected surgical instrument on the viewing screen; and
         (iii) directs the automated assistant to mechanically position the endoscope on the selected surgical instrument;
   activating the at least one operating key of the wearable wireless transmitter to transmit a first signal to the at least one wireless receiver;
   transmitting a second signal from the wireless receiver to the computer to select a surgical instrument on which to focus attention;
   displaying the selected surgical instrument on the viewing screen; and
   directing the automated assistant to mechanically position the endoscope on the selected surgical instrument.

2. The method according to claim 1, further comprising displaying the selected surgical instrument on the viewing screen after the automated assistant positions the endoscope on the selected instrument.

3. The method according to claim 1, wherein activating the at least one operating key is done manually by the user to activate the wearable operator.

4. The method according to claim 1, further comprising locating a position of a surgical instrument by activating the wearable operator by activating the operating key.

5. The method according to claim 1, wherein transmitting a second signal from the wireless receiver identifies at least one surgical instrument.

6. The method according to claim 1, further comprising wearing the wearable operator on a predetermined body part.

7. The method according to claim 6, wherein the predetermined body part is selected from the group consisting of a hand, at least one finger, at least one thigh, a neck, at least one leg, at least one knee, a head, and combinations thereof.

8. The method according to claim 6, further comprising, prior to wearing the wearable operator, selecting the wearable operator from the group consisting of a ring, a bracelet, and a combination thereof.

9. The method according to claim 1, wherein an action of activating the at least one operating key is selected from the group consisting of clicking, double clicking, pressing, depression, prolonged depression, voice activation, and combinations thereof.

* * * * *